(12) United States Patent
Pande et al.

(10) Patent No.: US 8,715,944 B2
(45) Date of Patent: *May 6, 2014

(54) FLUOROCHROMES FOR ORGANELLE TRACING AND MULTI-COLOR IMAGING

(75) Inventors: Praveen Pande, Holbrook, NY (US); Yuejun Xiang, Bayside, NY (US); Wayne Forrest Patton, Dix Hills, NY (US)

(73) Assignee: Enzo Life Sciences, Inc., Farmingdale, NY (US)

(*) Notice: Subject to any disclaimer, the term of this patent is extended or adjusted under 35 U.S.C. 154(b) by 1088 days.

This patent is subject to a terminal disclaimer.

(21) Appl. No.: 12/287,882

(22) Filed: Oct. 13, 2008

(65) Prior Publication Data

US 2010/0062460 A1  Mar. 11, 2010

Related U.S. Application Data

(63) Continuation-in-part of application No. 12/231,988, filed on Sep. 8, 2008.

(51) Int. Cl.
| | | |
|---|---|---|
| *G01N 33/53* | (2006.01) | |
| *G01N 33/567* | (2006.01) | |
| *C07C 211/00* | (2006.01) | |
| *C07C 223/00* | (2006.01) | |
| *C07C 221/00* | (2006.01) | |

(52) U.S. Cl.
USPC .................. 435/7.2; 564/336; 564/344

(58) Field of Classification Search
None
See application file for complete search history.

(56) References Cited

U.S. PATENT DOCUMENTS

| 6,140,500 A | * | 10/2000 | Yan et al. ............... 544/99 |
| 6,291,203 B1 | * | 9/2001 | Poot et al. ............... 435/40.5 |
| 2010/0062429 A1 | * | 3/2010 | Patton et al. ............... 435/6 |

OTHER PUBLICATIONS

Huange et al. Bioorg. Med. Chem. 13 (2005) 1435-1444.*

* cited by examiner

*Primary Examiner* — Clinton Brooks
(74) *Attorney, Agent, or Firm* — Anna D. DiGabriele Petti, Esq.

(57) ABSTRACT

Provided are compounds, methods and kits for identifying in cells of interest organelles including nuclei and a wide variety of organelles other than nuclei (non-nuclear organelles), as well as cell regions or cell domains. These compounds and methods can be used with other conventional detection reagents for identifying the location or position or quantity of organelles and even for distinguishing between organelles in cells of interest.

14 Claims, 13 Drawing Sheets

SCHEME FOR SYNTHESIS OF COMPOUND 43

FLUOROCHROMES FOR ORGANELLE TRACING AND MULTI-COLOR IMAGING

RELATED APPLICATIONS

This application is a continuation-in-part of U.S. patent application Ser. No. 12/231,988, filed on Sep. 8, 2008. This application claims priority to the aforementioned Ser. No. 12/231,988, the contents of which are also incorporated herein by its entirety.

FIELD OF THE INVENTION

This invention relates to fluorescent dyes and fluorescent compounds useful for identifying organelles in live and dead cells, including nuclei and organelles other than nucleic (non-nuclear organelles. More particularly, this invention relates to the identification of subcellular organelles, cell domains, cell regions, and the like, within living cells or extracellularly, with the identifying fluorescent dye or fluorescent compound retained within or otherwise localized to the specific subcellular organelles, cell domains or cells regions.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

As genetically encoded reporter molecules, fluorescent proteins have demonstrated applicability and versatility as molecular and cellular probes in life sciences and biomedical research. Among patents relating to fluorescent protein technology are U.S. Pat. Nos. 5,491,084, 5,625,048, 5,777,079, 5,804,387, 5,968,738, 5,994,077, 6,027,881, 6,054,321, 6,066,476, 6,077,707, 6,124,128, 6090,919, 6,172,188, 6,146,826, 6,969,597, 7,150,979, 7,157,565, 7,166,444, 7,183,399 and 7,297,782, references incorporated herein.

Fluorescent protein fusion to a gene promoter has been employed for reporting or verifying gene expression. Fluorescent protein fusion to a gene of interest has also been used to track a protein as it traverses a cell. If the fusion partner is a structural protein, then information pertaining to cellular architecture may be obtained. Fluorescent proteins have found application in a vast array of experiments, included those relating to monitoring gene promoter activity, gene expression levels, organelle dynamics, cellular architecture, gene expression timing, protein translocation, G-protein-coupled receptor (GPCR) activity, cell lineage, apoptosis, protein degradation, genotoxicity and cytotoxicity.

Cell-based assays are increasingly gaining in popularity in the pharmaceutical industry due to their high physiological relevance. Additional advantages include their ability to predict compound usefulness, evaluate molecular interactions, identify toxicity, distinguish cell type-specific drug effects, and determine drug penetration. Cell-based assays are relevant throughout the drug discovery pipeline, as they are capable of providing data from target characterization and validation to lead identification (primary and secondary screening) to terminal stages of toxicology. Current industry trends of performing drug screening with cell context demand easily monitored, non-invasive reporters. Fluorescent proteins fulfill this demand more completely than any other available tools. Requirements for advanced screening assays are driven by the objective of failing candidate compounds early in the drug discovery pipeline. This fundamental approach increases efficiency, reduces costs, and results in shorter time to market for new drugs. In order to fail compounds early, information-rich data for accurate early-stage decision making is required. Such data may be derived by screening compounds in context, that is, by screening in relevant living systems, rather than with classical biochemical assays, often incorporating sophisticated imaging platforms, such as high-content screening (HCS) workstations. The industrialization of fluorescent microscopy has led to the development of these high-throughput imaging platforms capable of HCS. When coupled with fluorescent protein reporter technology, HCS has provided information-rich drug screens, as well as access to novel types of drug targets.

As industry trends advance toward analysis in living systems (e.g. cells, tissues, and whole organisms), fluorescent proteins, by virtue of their non-invasive, non-destructive properties, are becoming indispensable tools for live-cell analysis. A broad range of fluorescent protein genetic variants are now available, with fluorescence emission profiles spanning nearly the entire visible light spectrum. Mutagenesis efforts in the original jellyfish *Aequorea victoria* green fluorescent protein have resulted in new fluorescent probes that range in color from blue to yellow and these are some of the most widely used in vivo reporter molecules in biological research today. Longer wavelength fluorescent proteins, emitting in the orange and red spectral regions, have been developed from the marine anemone *Discosoma striata* and reef corals belonging to the class Anthozoa. Other species have also been mined to produce similar proteins having cyan, green, yellow, orange, red, and even far-red fluorescence emission.

Recent emphasis on multi-color imaging in HCS has created renewed demand for easily measured, non-invasive, and non-disruptive cellular and molecular probes. With the increasingly expanding repertoire of fluorescent proteins has come increased demand for complementary reagents, such as organic fluorochrome counter-stains that augment analysis by providing information relating to co-localization of the fluorescent proteins to various organelles and subcellular targets. To date, however, concerted efforts in developing such organic fluorochromes, specifically tailored to working in concert with fluorescent proteins, has been limited in scope. The application of fluorescent proteins and of organic fluorochromes is not an either/or proposition. Each technology has distinct advantages and limitations. These two technologies can be optimized and combined to work in concert, however, in order to maximize the information content obtained from fluorescence microscopy- and imaging-based screening approaches. By doing so, achieving rich multi-dimensional physiological information can be obtained.

While suitable for analysis of cell surfaces and permeabilized cells, fluorescently-labeled antibodies have few practical applications for intracellular imaging in living cells, due to their inherent inability to penetrate to their targets, which has given rise to development of cell-permeable small molecule organic fluorochromes, certain ones of which naturally sequester inside-specific organelles, based upon biophysical or biochemical properties favoring that distribution. Acceptable small molecule organic probes for cell imaging and analysis need to be minimally perturbing, versatile, stable, easy-to-use, and easy to detect using non-invasive imaging equipment. A problem with the classical organic probes from histology is that many of them require cofactors or, by requiring fixation or staining, report only on the static condition of a dead cell. The required additional steps may be time consuming and expensive and, in the case of fixing and staining, may lack biological relevance. In the context of the analyses described above, an organic probe must be able to report upon events in living cells and in real time. Simplicity is of key importance, especially in the context of drug screening.

While various organic fluorochromes have been developed in the past for live cell analysis, typically they were not devised with optimization of performance in conjunction with the wide palette of available fluorescent proteins in mind. For instance, several U.S. patent documents (U.S. Pat. Nos. 5,338,854, 5,459,268, 5,686,261, 5,869,689, 6,004,536, 6,140,500 and 6,291,203 B1, as well as US Patent Applications 2005/0054006 and 2007/0111251 A1, references incorporated herein) disclose organic fluorochromes which are described as useful for visualizing membranes, mitochondria, nuclei and/or acidic organelles. Additional examples of various fluorochromes and their application in biological imaging may be found in the published literature (see, for example, Pagano et al, 1989; Pagano et al, 1991; Deng et al, 1995; Poot et al, 1996; Diwu et al, 1999; Rutledge et al, 2000; Lee et al, 2003; Bassøe et al, 2003; Rosania et al, 2003; Li et al 2007; Boldyrev et al, 2007; Nadrigny et al, 2007). These dyes have been created using a number of fluorophores, most commonly dipyrromethene boron difluoride (BODIPY), cyanine, carbocyanine, styryl and diaminoxanthene core structures. Typical emission maxima for these organic fluorophores span from 430 to 620 nm. Many of the dyes consequently occupy valuable regions of the visible emission spectrum that preclude use of various fluorescent proteins. By doing so, their use limits the overall levels of multiplexing achievable in HCS assays. Additionally, these dyes often display other suboptimal properties, such as a propensity to photo-bleach, metachromasy and even a tendency to photo-convert to different emission maxima upon brief exposure to broad-band illumination.

Artifacts Associated with Previously Devised Organic Fluorochromes for Live Cell Analysis Fluorescence co-localization imaging is a powerful method for exploring the targeting of molecules to intracellular compartments and for screening of their associations and interactions. In these kinds of experiments, distinct fluorochromes and/or fluorescent proteins of interest are imaged as spectrally separated detection channels. The fluorescence intensity in each channel is ideally dominated by spatial and concentration information derived from one fluorophore only. Many commercially available organic fluorophores for subcellular analysis are disadvantaged in displaying suboptimal properties relating to these types of applications.

Lysotracker Red DND-99 (Invitrogen, Carlsbad, Calif.) contains a BODIPY fluorophore in the form of a conjugated multi-pyrrole ring structure and also contains a weakly basic amine that causes the fluorochrome to selectively accumulate in acidic compartments, exhibiting red fluorescence upon appropriate illumination (excitation: 577 nm, emission: 590 nm) (Freundt et al, 2007). Lysotracker Red is structurally related to Lysotracker Green but the former has an additional pyrrole ring in conjugation with the primary structure, which produces a longer wavelength emission. Lysotracker Red has commonly been used in multi-color imaging studies as a lysosomal marker to determine intracellular localization of GFP-tagged proteins by fluorescence or confocal microscopy. Excitation of the red-emitting molecule with broad-band illumination induces, however, molecular changes rendering its photochemical properties similar to those of Lysotracker Green. The similarities between the spectra of Lysotracker Green and converted Lysotracker Red suggest that the third pyrrole ring is taken out of conjugation during the photo-conversion process, leading to a shorter wavelength dye emission. Thus, Lysotracker Red staining for epifluorescence or confocal microscopy, in conjunction with visualization of GFP, leads to spurious results due to photo-conversion of the fluorophore (Freundt et al, 2007).

Acridine orange (Sigma-Aldrich, Saint Louis, Mo. and other sources) has also been used extensively as a fluorescent probe of lysosomes and other acidic subcellular compartments. Acridine orange's metachromasy results, however, in the concomitant emission of green and red fluorescence from stained cells and tissue (Nadrigny et al, 2007). Evanescent-field imaging with spectral fluorescence detection, as well as fluorescence lifetime imaging microscopy demonstrate that green fluorescent acridine orange monomers inevitably coexist with red fluorescing acridine orange dimers in labeled cells. The green monomer emission spectrally overlaps with that of GFP and produces a false apparent co-localization on dual-color images. Due to its complicated photochemistry and interaction with cellular constituents, acridine orange is a particularly problematic label for multi-color fluorescence imaging-both for dual-band and spectral detection. Extreme caution is required, therefore, when deriving quantitative co-localization information from images of GFP-tagged proteins in cells co-labeled with acridine orange.

In principle, the styryl dye, FM4-64 (Invitrogen, Carlsbad, Calif.) is useful for studying endocytosis and vesicular recycling because it is reputed to be confined to the luminal layer of endocytic vesicles. This particular dye distributes throughout intracellular membranes and it indiscriminately stains both the endoplasmic reticulum and nuclear envelope (Zal et al, 2006). However, though the different pools of dye all emit at roughly 700 nm, a spectral shift in fluorescence excitation maximum is observed wherein the dye present in endocytic vesicles and the endoplasmic reticulum absorbs at 510 nm, while the dye associated with the nuclear matrix absorbs at 622 nm. While this can be used advantageously in order to selectively image the nuclear membrane, in certain multi-parametric imaging experiments the dual absorption properties can be problematic. The shift in peak of the absorption spectrum is not confined to FM dyes. A similar phenomenon has also been reported for Rhodamine 6G, where the dye's absorbance maximum is red-shifted from 527 to 546 nm in a concentration dependent manner (Johnson et al, 1978). Rhodamine 6G is commonly employed to label leukocytes, especially in vascular injury models.

Fluorescent analogs of ceramide are commonly employed to visualize golgi bodies in live cells. The fluorescence emission maximum of certain BODIPY-labeled ceramides, such as $C_5$-DMD-Ceramide (a.k.a. C5-BODIPY-Cer, Invitrogen, Carlsbad, Calif.), has been shown to depend strongly upon the molar density of the probe in the membrane, shifting in emission maximum from green (~515 nm) to red (~620 nm) with increasing concentration (Pagano et al, 1991). Consequently, in live cells, the Golgi bodies display yellow/orange fluorescence emission (a combination of red and green fluorescence emission), whereas predominantly green fluorescence emission is observed in the endoplasmic reticuli, the nuclear envelope and mitochondria. Co-localization studies with GFP are compromised, therefore, when employing these fluorescent ceramide analogs, due to their inherent dual emission characteristics.

Only in the specific instance of nuclear staining have the aforementioned problems been alleviated to a large extent. DRAQ5™ ([1,5-Bis[[2-(dimethylamino)ethyl]amino]4,8-dihydroxyanthracene-9,10-dione], Biostatus Limited, UK) is a cell-permeable substituted anthraquinone dye designed for use in a range of fluorescence detection technologies, for the discrimination of nucleated cells (U.S. Pat. Nos. 6,468,753 B1 and 7,060,427 B2, Smith et al, 1999; 2000). The dye permits nuclear discrimination and functional assays to be performed in live cells in combination with a variety of UV and visible range fluorochromes, such as fluorescein, R-phycoerythrin and the GFP super-family. Additionally, the dye has little propensity to photo-bleach.

In U.S. patent application Ser. No. 12/231,988 (filed on Sep. 8, 2008), several useful compounds and methods are disclosed for organelle tracing and multi-color color imaging. The present invention provides yet other novel compounds similarly useful for such organelle tracing and multi-color imaging.

SUMMARY OF THE INVENTION

The present invention provides a compound comprising the structure

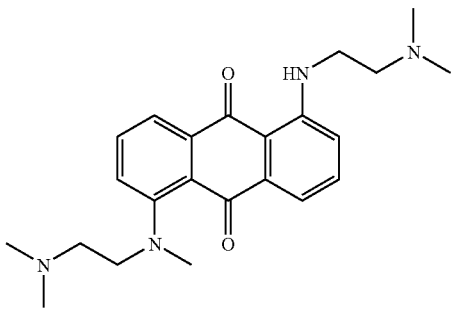

The present invention also provides a compound comprising the structure

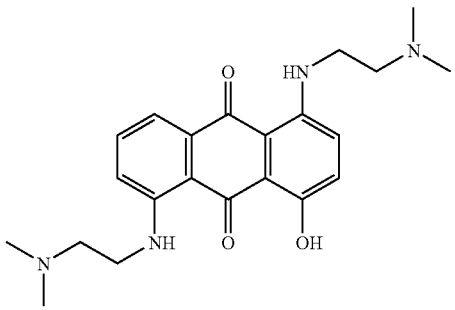

Also provided by this invention are methods and kits for use of these compounds, including methods and kits for identifying the location or position of nuclei and for total cell staining using the compounds above.

DESCRIPTION OF THE INVENTION

Figure 1:
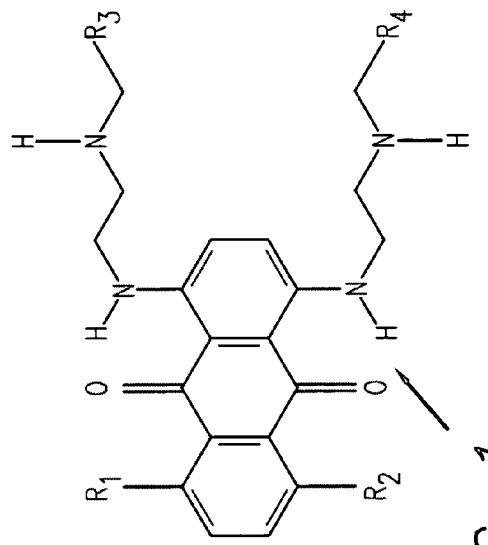
FIG. 1: Example of bioisoteric anthraquinone fluorochrome structures emitting in the green and far-red regions of the visible light spectrum.
Figure 2:
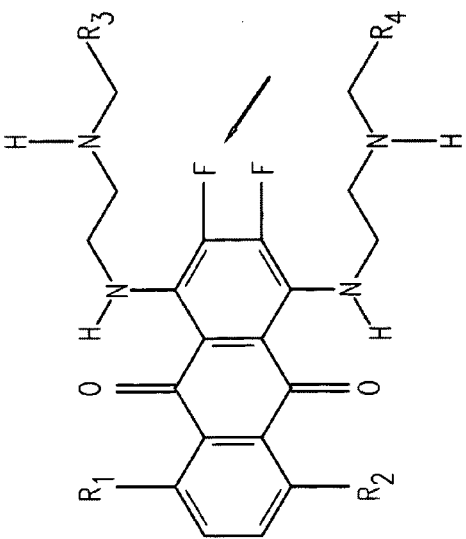
FIG. 2: Example of bioisoteric anthraquinone fluorochrome structures emitting in the red and far-red regions of the visible light spectrum.

One of the major challenges in the creation of fluorescent dyes as cell-permeable probes is to generate fluorophores that fluoresce strongly in aqueous media, particularly above 600 nm or at even longer wavelengths. Motivation for research in this area is drawn from needs for intracellular, tissue, and whole organism imaging. The present invention provides a family of far-red emitting cell-permeable small molecule organic probes that spontaneously localize to specific subcellular organelles, cell domains and cell regions which can be readily used in combination with other commonly used UV- and visible excitable organic fluorochromes and fluorescent proteins in multi-color imaging and detection applications. Most importantly, many of the organic probes of the present invention do not occupy valuable regions of the visible emission spectrum utilized by the common UV and visible range fluorochromes and fluorescent proteins, most particularly green fluorescent protein (GFP) and the fluorescent protein super-family. These organic probes can then be used in concert with the other fluorochromes to report drug or compound effects in the dynamic context of the living whole cell.

Definitions:

By fluorescence is meant the emission of light as a result of absorption of light-emission, occurring at a longer wavelength than the incident light.

By fluorophore is meant a component of a molecule which causes a molecule to be fluorescent.

By fluorochrome is meant any of a group of fluorescent dyes used to stain biological specimens.

By anthraquinone is meant the quinone derivative of anthracene, a tricyclic aromatic hydrocarbon containing two opposite carbonyl groups (C═O) at the 9, 10 positions of anthracene. These compounds may also be referred to as anthracenediones or as 9,10-dioxoanthracenes.

By aza-anthraquinone is meant a heterocyclic compound structurally related to anthraquinone, bearing either one (mono-aza) or two (di-aza) nitrogen atom substitutions in the anthracene framework.

By anthrapyrazole is meant a derivative of anthraquinone in which a pyrazole ring is fused to the anthraquinone core structure in order to generate a tetracyclic ring system.

By aza-anthrapyrazole is meant a derivative of aza-anthraquinone in which a pyrazole ring is fused to the aza-anthraquinoine core structure in order to generate a tetracyclic ring system.

By benzophenoxazine is meant a phenoxazine core structure that has been extended through addition of a fused benzene ring. Benzophenoxazines may be 'angular' or 'linear' depending upon the orientation of the ring fusion.

By metachromasy is meant the hypsochromic (shift in absorption to shorter wavelength) and hypochromic (decrease in intensity of emitted fluorescence) change in color exhibited by certain dyes in aqueous-based media under conditions such as: (1), increase in dye concentration; (2), temperature decrease; (3), salting out; and (4), interaction with substrates that favor water intercalation and/or proximity or stacking of dye monomers.

By bioisosterism is meant substituents or groups with similar physical or chemical properties that impart similar biological properties to a chemical compound. The purpose of exchanging one bioisostere for another is to enhance the desired biological or physical properties of a compound without making significant changes in chemical structure.

Basic Fluorophore Core Structures:

The present invention pertains to the preparation and use of fluorescent dyes comprising polycyclic fused ring systems, such as anthraquinone, anthrapyrazole, and benzophenoxazine fluorophores as well as their aza derivatives in cell imaging and detection. Generally, these types of dyes are electrically neutral and lipophilic, properties which permit them to be better solubilized in non-polar environments, such as cell membranes thereby rendering them cell permeable. More particularly, the invention relates to modifications of these dyes with functional groups that target the dyes to various subcellular organelles or regions. In one embodiment of the present invention, the functional groups attached to the dyes do not have a propensity for a particular organelle or region in and of themselves, but their addition to a dye endows the modified dye with such properties. In another embodiment of the present invention, functional groups are added that intrinsically have their own affinity for a particular organelle or region and the addition of such groups to a dye conveys this property to the dye.

In the present invention, the cell-permeable fluorescent dyes may also be described by the following general formulas:

The present invention provides for a dye having the formula:

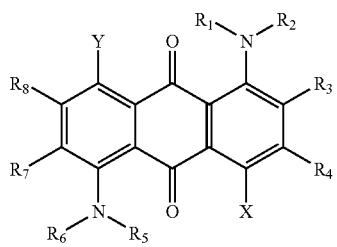

wherein each of X, Y, $R_3$, $R_4$, $R_7$, and $R_8$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^-$), a thiophosphate monoester ($PSO_2^-ER_{11}$), a thiophosphate diester ($PSOER_{11}ER_{12}$), a thiophosphonate ($PSO_2^-$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$, $R_2$, $R_5$ and $R_6$ are independently H or-L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^-$), a thiophosphate monoester ($PSO_2^-ER_{11}$), a thiophosphate diester ($PSOER_{11}ER_{12}$), a thiophosphonate ($PSO_2^-$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer. When $R_1=R_3=R_4=R_5=R_7=R_8=H$; X and Y are OH, $R_2$ and $R_6$ contain -L-$NR_9R_{10}$, then $R_2=R_6$ and wherein when L is a $C_{2-8}$ alkylene group and $R_9$ and $R_{10}$ are independently selected from hydrogen, $C_{1-4}$ alkyl, $C_{2-4}$ hydroxyl-alkyl and $C_{2-4}$ aminoalkyl or $R_9$ and $R_{10}$ together form a $C_{2-6}$ alkylene group which with the nitrogen atom to which $R_9$ and $R_{10}$ are attached forms a heterocyclic ring.

The present invention also provides for a dye having the formula:

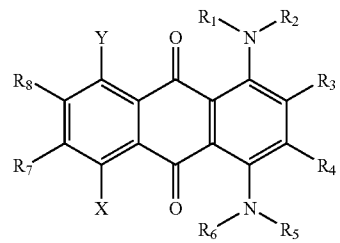

wherein each of X, Y, $R_3$, $R_4$, $R_7$, and $R_8$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$, $R_2$, $R_5$ and $R_6$ are independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^{-ER}{}_{11}$), a phosphate diester ($PO_2ER_{11}ER_{12}$), a phosphonate monoester ($PO_2^{-ER}{}_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer.

The present invention also provides for a dye having the formula:

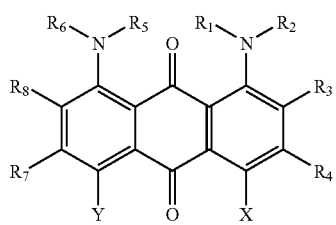

wherein each of X, Y, $R_3$, $R_4$, $R_7$, and $R_8$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a The present invention also provides for a dye based on an anthrapyrazole ring having the formula:

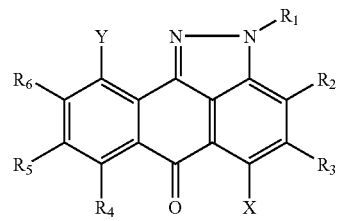

wherein each of X, Y, $R_2$, $R_3$, $R_4$, $R_5$ and $R_6$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$ is independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer.

The present invention also provides a dye based on a bis-anthrapyrazole ring having the formula:

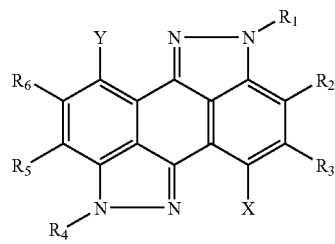

wherein each of X, Y, $R_2$, $R_3$, $R_5$ and $R_6$ are independently H, OH, F, Cl, Br, I, CN, sulfonate or its salt, sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), thioamide ($CSNR_{11}R_{12}$), an amino, a nitro, or an alkyl group wherein any of E can independently comprise O or S. The alkyl group is saturated or unsaturated, linear or branched, substituted or unsubstituted, an alkoxy group wherein the alkoxy group is saturated or unsaturated, branched or linear, substituted or unsubstituted. $R_1$ and $R_4$ are independently H or -L-Q wherein L is $C_{0-18}$ linker arm comprising carbon, sulfur, oxygen, nitrogen, or any combinations thereof, wherein the linker arm may be saturated or unsaturated, linear or branched, substituted or unsubstituted, or any combinations thereof. Q comprises a sulfoxide ($SOR_{11}$), a sulfone ($SO_2CR_{11}R_{12}R_{13}$), a sulfonamide ($SO_2NR_{11}R_{12}$), a phosphate monoester ($PO_3^-ER_{11}$), a phosphate diester ($PO_2ER_{11}ER_{12}$), a phosphonate monoester ($PO_2^-ER_{11}$), a phosphonate diester ($POER_{11}ER_{12}$), a thiophosphate ($PSO_3^=$), a thiophosphate monoester ($PSO_2^-ER_{11}$), a thiophosphate diester ($PSOER_{11}ER_{12}$), a thiophosphonate ($PSO_2^=$), a thiophosphonate monoester ($PSO^-ER_{11}$), a thiophosphonate diester ($PSER_{11}ER_{12}$), a phosphonamide ($PONR_{11}R_{12}NR_{14}R_{15}$), its thioanalogue ($PSNR_{11}R_{12}NR_{14}R_{15}$), a phosphoramide ($PONR_{11}R_{12}NR_{13}NR_{14}R_{15}$), its thioanalogue ($PSNR_{11}R_{12}NR_{13}NR_{14}R_{15}$), a phosphoramidite ($PO_2R_{14}NR_{11}R_{12}$), its thioanalogue ($POSR_{14}NR_{11}R_{12}$), ketone ($COR_{11}$), thioketone ($CSR_{11}$), amide ($CONR_{11}R_{12}$), or thioamide ($CSNR_{11}R_{12}$) wherein any of E can independently comprise O or S. Q can also comprise $ZR_9R_{10}$ wherein Z can be N, O, S, Se or any combinations thereof and wherein $R_9$ and $R_{10}$ can independently be hydrogen or an alkyl group wherein the alkyl group is saturated or unsaturated, linear or branched, substituted or unsubstituted, an alkoxy group that is saturated or unsaturated, branched or linear, substituted or unsubstituted, or when taken together, $R_9$ and $R_{10}$ may form a heterocyclic ring. Q can also comprise a substituted anthraquinone moiety such that the whole molecule is either a homo or hetero dimer.

The present invention provides a compound (designated Compound 41 in the Examples below) which comprises the structure

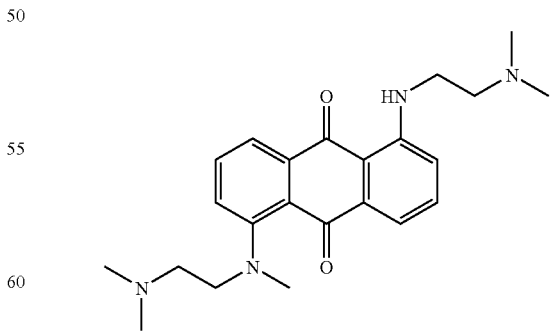

Compound 41 is particularly useful as a total cell stain.

The present invention also provides a compound (designated Compound 43 in the Examples below) which comprises the structure

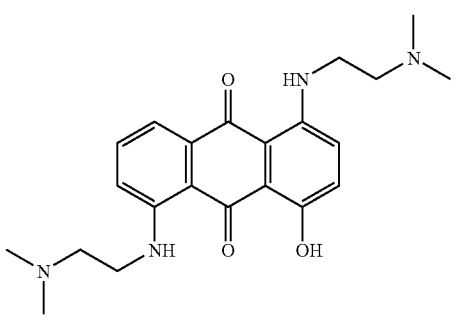

Figure 12:
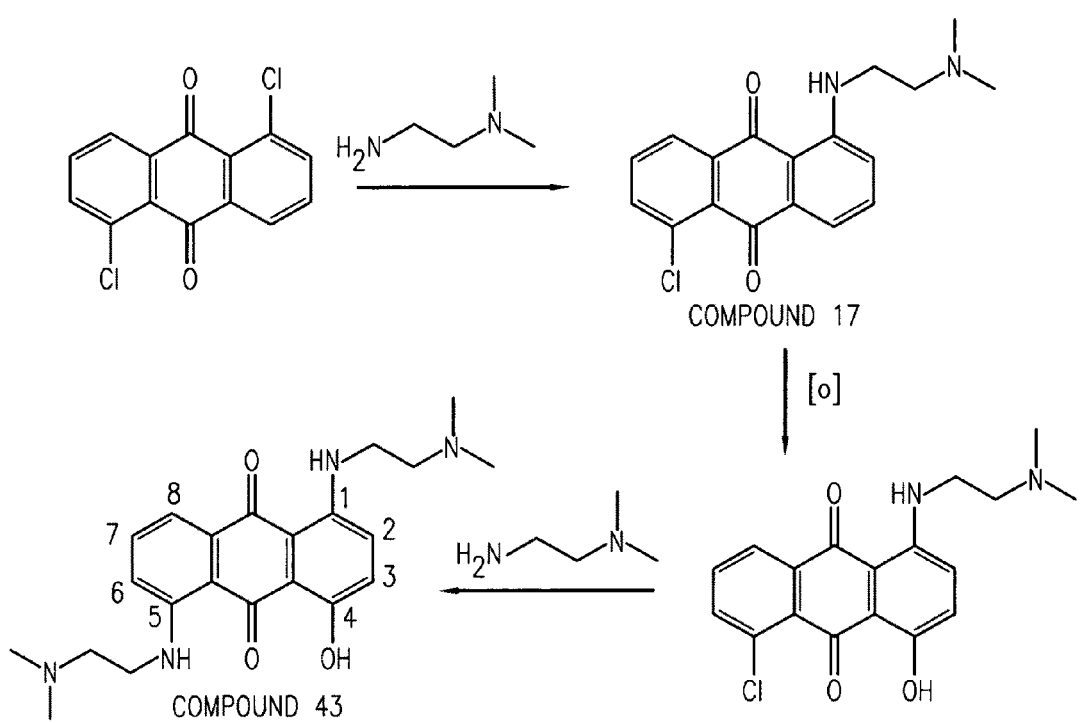
FIG. 12: Synthetic scheme for Compound 43

Compound 43 of the present invention can be prepared from commercially available reactants, utilizing synthetic methodologies well-known and routinely used by those skilled in the art of synthetic organic chemistry. The synthesis of Compound 43 is presented in the scheme provided in FIG. 12. Selective substitution of one chloro group of commercially available 1,5-dichloroanthraquinone with N,N-dimethylethylenediamine in dimethylacetamide provided Compound 17. The latter compound was then oxidized using sodium chlorate and sulfuric acid to provide the hydroxy derivative which was then treated with N,N-dimethylethylenediamine to provide Compound 43. This novel Compound 43 is useful in identifying nuclei location/position.

Also provided by this invention are methods of identifying the location or position of nuclei in cells and in samples containing cells and also for total cell staining using the compounds above. Any of the previously described components for fixing proteins, glycans and lipids, permeabilizing cell membranes, identifying fluorescent signals, detecting reagents are applicable to both compounds just described.

This invention also provides methods for quantifying signals from the nucleic or from the cells themselves. Again, any of the previously components for carrying out such methods are applicable to both of these compounds.

Referring to Compound 43 as described and illustrated further in the examples below, this novel compound provides advantages over the prior art Draq5 compound in that it can be used with several popular fluorescent proteins or fluorescent stains. Such fluorescent proteins and fluorescent stains include Cy5, Phycoerythrin-Cy5 (PE-Cy5), Alex Fluor dye (including Alexafluor 660 and Alexafluor 680) and Spectrum FarRed conjugates. In particular, Compound 43 has a clear advantage over DRAQ5 for multiplexing with far-red emitting as demonstrated in the Example below.

Also provided are kits for identifying cells of interest. Such a kit contains in packaged combination (A) the compound comprising the structure

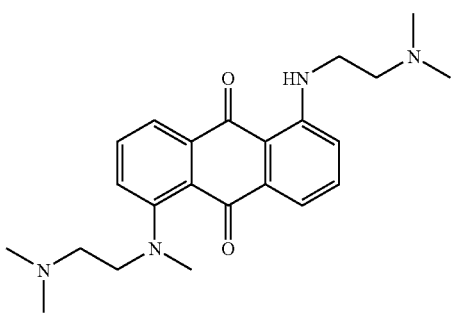

(B) buffers, wherein the compound (A) is at a working concentration; and (C) instructions or a protocol for recommended use of the kit. Alternatively, the kit may contain dilution buffers, fixative reagents, permeabilizing reagents, detection reagents, calibrants, wash solution, and the like, all of which have been previously described above.

Other kits provided by this invention are ones for identifying the location or position of nuclei in cells or in a sample containing cells of interest. These kits comprise in packaged combination (A) the compound comprising the structure

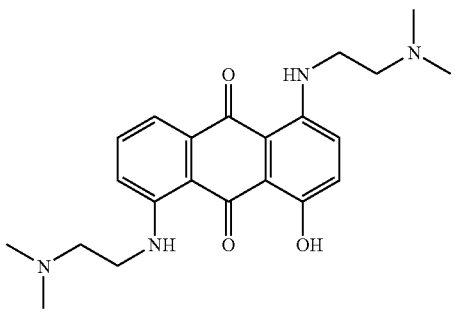

(B) buffers, wherein the compound (A) is at a working concentration; and (C) instructions or a protocol for recommended use of the kit. Alternatively, such a kit may contain other components or elements including dilution buffers, fixative reagents, permeabilizing reagents, detection reagents, calibrants, wash solution, and the like, all of which have been previously described above.

Spectral Properties

In one particular embodiment of the present invention, the preparation of cell-permeable, substituted anthraquinones are described, as well as their applications in a range of fluorescence imaging and detection technologies. Fluorochromes based upon this fluorophore core absorb maximally in the vicinity of 647 nm and emit maximally in the vicinity of 670 nm. These far-red emitting fluorochromes are thus particularly useful in multi-parametric imaging applications using a range of commonly available UV and visible light-excitable fluorochromes and fluorescent proteins. Fluorinated derivatives of this core structure are useful for shifting the excitation/emission profile of the fluorophore from the far-red to the red region of the visible spectrum. Aza-anthraquinones, based upon, for example, a 9(10H)-acridanone or benz[g]isoquinoline-5,10-dione core structure, may also find use in the present invention although the presence of nitrogen atom substitutions in the anthracene framework shifts the fluorescence emission characteristics of the compounds, so as they emit maximally at roughly 400430 nm. These compounds can find application in multi-color imaging applications, especially in conjunction with turquoise-, green-, red- and far-red-emitting dyes.

This invention further pertains to the preparation and use of other cell-permeable substituted anthrapyrazoles containing carbocyclic or heterocyclic fluorophores. Fluorochromes based upon this fluorophore core absorb maximally in the vicinity of 410 nm and emit maximally in the vicinity of 520 nm. Emission of these fluorophores may also be shifted to shorter wavelengths through addition of fluorine atoms to the core fluorophore structure.

While being green-emitting rather than far red-emitting fluorophores, and thus emitting in a valuable region of the light spectrum overlapping other common green-emitting fluorochromes such as fluorescein and GFP, the anthrapyrazoles have other favorable properties relative to conventional fluorophores, such as BODIPY-FL, most particularly high resistance to photo-bleaching. Nuclear-targeting anthrapyrazoles offer performance advantages relative to blue-emitting dyes, such as DAPI and the Hoescht dyes for live cell imaging since emission that is distinct from intracellular NADH and FADH autofluorescence is achieved and the requirement for specialized UV-emitting laser sources is avoided, especially important in flow cytometry applications.

The green-emitting anthrapyrazoles are also suitable for use in combination with the described red- and far red-emitting anthraquinones of the present invention in multi-parametric analyses. The green- or far red-emitting fluorophores may be used in combination with red-emitting, yellow-emitting and/or blue-emitting fluorochromes or fluorescent proteins for multi-parametric analyses. Fluorescent cell-permeable, substituted benzophenoxazine dyes are also valuable for highlighting subcellular organelles, domains and regions. Benzo[a]phenoxazine, benzo[b]phenoxazine and benzo[c] phenoxazine are all suitable core fluorophore structures for substitution of organelle-targeting groups. Chemical substituents that freely donate and/or accept electron density on benzophenoxazine core structures can, in some orientations, provide fluorescent compounds, as well as target the core structure to various regions of live cells. Such probes typically have high fluorescence quantum yields, especially in more apolar environments and certain ones can fluoresce in the far-red region of the visible spectrum. These dyes exhibit higher photostability as compared to other classes of dyes used conventionally in cell imaging, such as the BODIPY dyes.

Affinity Properties

Certain anthraquinones, anthrapyrazoles and benzophenoxazines are known to intercalate into DNA and interact with topoisomerase II, thereby inhibiting DNA replication and repair as well as RNA and protein synthesis. A large body of literature also exists with regard to their use in the treatment of cancer presumably due to the foregoing mechanism or other properties relating to intercalation. Due to their affinity for nucleic acids, these dyes have also found use with in vivo and in vitro methods where advantage is taken of their high level of specificity for nuclear staining. It has been unexpectedly found that the presence of various modifications on the core structures can alter the affinity of such molecules so that they can be used to identify organelles other than the nucleus. Thus, even though neither the modification group(s) or the dye have an affinity for the non-nuclear organelle, the modified dye exhibits this property. The use of various groups to alter the affinity of dyes towards a variety of different organelles has been described previously (Rosania et al., 2003 J Am Chem. Soc 125; 1130-1131 and Lee et al., 2003 Chem Commun 1852-1853) but these efforts involved styryl dyes that did not have any particular organelle affinity in and of themselves. In contrast, the present invention describes the alterations of dyes whose cores structures are known to have a nuclear affinity and redirecting them to a different organelle or suborganelle locus.

Typically, endoplasmic reticuli-targeting anthraquinone, anthrapyrazole and benzophenoxazine probes tend to be amphipathic, lipophilic cations with moderate-sized conjugated systems (This particular condition being met by the fluorophore core itself. Without wishing to be bound by theory, it appears that their moderately lipophilic character permits probe uptake by passive diffusion without nonspecific accumulation in biological membranes. The moderately amphipathic character favors uptake into the endoplasmic reticuli, perhaps owing to high concentrations of zwitterionic lipid head-groups in the organelle. Cationic amphiphilic anthraquinones, anthrapyrazoles and benzophenoxazines containing a basic moiety often accumulate in lysosomes or other acidic subcellular compartments. This lysosomotropism is thought to be due to the protonation of the dye within acidic organelles leading to the formation of a membrane-impermeable form. Highly lipophilic dyes show a greater propensity to accumulate in lysosomes than those with a lower lipophilicity. Selective mitochondrial accumulation involves electric potential, ion-trapping, and complex formation with cardiolipin. The basic mechanism for accumulation of mitochondrial probes relies upon their chemical structure, consisting of highly conjugated moieties that extensively delocalize a positive charge, thus allowing electrophoretic uptake toward the negatively charged matrix phase of the polarized inner mitochondrial membrane. However, although lipophilic cations are regarded as the most common mitochondriotropic dyes, electrically neutral and even potentially anionic dyes may accumulate in the mitochondria. Physicochemical features of probes which favor nucleic acid binding include cationic character and a planar aromatic system above a minimum size (This particular condition being met by the fluorophore core itself. Features which reduce accumulation in non-nuclear sites include high base strength and hydrophilicity of the cation.

While general guidelines for creating organelle-targeting anthraquinone, anthrapyrazole and benzophenoxazine probes can be provided, the basis of the selectivity of specific fluorochromes for various subcellular organelles, regions or domains in live cells is sometimes elusive. To clarify this, interactions of living cells with series of different anthraquinone, anthrapyrazole or benzophenoxazine molecules, having systematically varied physicochemical properties, should be analyzed experimentally and numerically using approaches such as quantitative structure activity relationship analysis (QSAR) and Fick-Nernst-Planck analysis. Typically, a single cell line or a panel of cell lines is incubated with different concentrations (typically 1-100 µM) of the potential organelle-targeting compounds and subcellular distribution is monitored by wide-field fluorescence microscopy. Combinatorial synthesis of panels of anthraquinone, anthrapyrazole or benzophenoxazine derivatives may be subjected to cell-based screening in order to identify lead compounds with desired localization properties.

Dyes Conjugated to Organelle Specific Moieties

In another embodiment of the present invention, we have found that the combination of nuclear dye with a moiety that has an affinity for a locus other than the nucleus can result in a conjugate that retains the ability to target the non-nuclear organelle and endowing it with the spectral properties of the dye. It has been found that a variety of subcellular organelle, region or domain targeting functional groups may be covalently affixed to the anthraquinone, anthrapyrazole or benzophenoxazine core. Typically, either one or two such functional groups are affixed to the core structure, though in certain circumstances as many as four such groups can potentially be affixed to the fluorophore core. These are non-limiting examples of targeting groups that may find use with the present invention by being conjugated to an anthraquinone, anthrapyrazole or benzophenoxazine.

TABLE 1

Examples of functional groups (moieties) useful for generating fluorescent anthraquinone, anthrapyrazole and benzophenoxazine conjugates that are applicable to live cell imaging.

| Functional group (Moiety) | Subcellular target |
| --- | --- |
| γ-aminobutyryl atractyloside | ADP/ATP carrier in membranes |
| β-glucosamine | Lysosomes |
| alkyl amines, alkyl amine N-oxides, aliphatic amines, aliphatic amine N-oxides | Nucleus |
| brefeldin A | Endoplasmic Reticulum |
| cadaverine | Lysosome |
| ceramide | Golgi Body |
| cerebroside | Plasma membranes |
| colcemid or colchicine | Microtubule network |
| cycloheptaamylose | Cell surfaces |
| erythromycin | Bacterial ribosomes |
| galactoside | Bacterial membrane vesicles. |
| galactosyl, glycosyl or lactosyl ceramide | Endosome/Lysosome |
| ganglioside | Golgi Body |
| glibenclamide | Mitochondria |
| Guanidine, biguanidine | Mitochondria |
| glutathione | Microsomes |
| isocolchicine | Microtubule network |
| Mitochondrial localization sequence (MLS) peptides (e.g. MLSLRQSIRFFKGC, MSVLTPLLLRGLTGSARRLPVPRAKIHSL) | Mitochondria |
| mycolactone | Cytoplasm |
| N-(Acyl)-Sphingosines | Golgi Body |
| N-ε-D, L-lysine | cholesterol-free domains in membranes |
| N-acylcholines | Cholinergic receptors in membranes |
| norhexestrol and hexestrol | Estrogen-binding proteins in membranes |
| nystatin | Membranes |
| paclitaxel | Microtubule network |
| pentane | Lysosomes |
| Phallacidin or phalloidin | Microfilament network |
| phosphatidylcholine or phosphatidylethanolamine | Membranes |
| polymyxin | Lipopolysaccharide and lipid A in bacteria |
| propranolol | Calcium-magnesium-ATPase in membranes |
| protamine | Mucopolysaccharide layers |
| ryanodine | Nuclear envelope |
| spermidine and spermine | Endosomes |
| steroid (e.g. cholesterol, coprostanol) | Lipid rafts |
| taurine | Basolateral membrane |
| thapsigargin | Nuclear envelope |
| trimethylammonia | Basolateral organic cation transporters of proximal tubule |
| vinblastine | Mitochondria |

Conjugation may take place with an organelle specific moiety in combination with an anthraquinone, anthrapyrazole or benzophenoxazine that in unconjugated form accumulates in the nucleus, or contrariwise, the dye may be a modified version, as described above, such that both the organelle specific moiety and the dye have an affinity for the same organelle, thereby potentially increasing the specificity of the conjugate to the organelle of interest.

Inclusion of Spacer Groups for Substituted Anthraquinone, Anthrapyrazole and Benzophenoxazine Probes:

In some cases it is advisable to employ an intervening spacer group (a.k.a. linker region) in order to ensure biological targeting of the anthraquinone, anthrapyrazole or benzophenoxazine probe. The spacer group minimizes steric interference between the organelle-targeting group and the fluorophore. For example, a hexanoic spacer group may be used between the anthraquinone moiety and the organelle-targeting functional group. This spacer may be created using a compound such as 6-amino hexanoic acid. In other instances a methyl-, ethyl-, propyl-, butyl-, pentyl-, hexyl-, heptyl, or octyl-methylene spacer may be required. Piperazine, 1-(2-aminoethyl) piperazine, ε-aminohexanoyl and ε-aminocaproyl are also suitable spacer groups in some instances. The length of the spacer group may vary from a single methylene residue to a long polymer, employing such spacers as poly(ethylene glycol), for example. Aliphatic or hetero-aliphatic spacer groups may be employed, as can peptide-, oligonucleotide-, or peptide nucleic acid-based spacer groups.

Probes for lipid microdomains, or rafts that have formed as a result of specific lipid-lipid or lipid-protein interactions in the cell membrane, are important tools for analysis of the regulation of signal transduction, cellular transport, and lipid sorting. A specific example of domain-targeting anthraquinone, anthrapyrazole or benzophenoxazine probes requiring spacer groups are cholesteryl esters, in which a fluorophore is esterified to the $C_3$-hydroxy group of the sterol. Without wishing to be bound by theory, it appears that bending or looping of a flexible acyl linker region is required in order for such probes to effectively intercalate into lipid rafts in the plasma membrane. Alternatively, when creating free cholesterol-dye conjugates, different linkers may be used to couple the fluorophore to the sterol's aliphatic side chain. The cholesterol ester derivatives require much longer linkers ($\sim C_{10}$-$C_{12}$ alkyl chains) than the free cholesterol derivatives ($\sim C_1$-$C_3$ alkyl chains) to achieve biologically active compounds. The structure of the linker region used to ligate the anthraquinone, anthrapyrazole or benzophenoxazine moiety to the $C_3$-hydroxyl or aliphatic side chain of the sterol, is an important determinant of the ability of the probe to partition into liquid-ordered versus liquid-disordered membrane domains.

Formulations and Compositions

Compositions according to the invention comprise a compound of the invention and are intended to include any and all solvents, dispersion media, coatings, isotonic and absorption delaying agents, and the like, compatible with the application. Except insofar as any conventional media or agent is compatible with the active compound, such media can be used in the compositions of the invention. Supplementary active compounds can also be incorporated into the compositions.

For example, when a composition of the invention is applied to cells or tissues, it is formulated to be compatible with the intended route of entry into the cells or tissues. For example, isotonic saline solutions, mildly hypertonic saline solutions, phosphate-buffered saline, cell culture media, isotonic sucrose solutions, or mildly hypertonic sucrose solutions may serve as the vehicle for delivery of the compound to the cells. Polyethylene glycols, glycerin, dimethylsulfoxide, dimethylformamide, propylene glycol, or other co-solvents may be included to facilitate solubilization of the compound. Antibaterial agents, such as benzyl alcohol or methyl parabens; antioxidants, such as ascorbic acid or sodium bisulfite; chelating agents, such as ethylenediaminetetraacetic acid (EDTA) or cyclodextrin; buffers, such as acetates, phosphates or citrates; agents for adjusting tonicity, such as sodium chloride or sucrose; and agents that adjust the pH value of the delivery vehicle, such as sodium hydroxide and hydrochloric acid may be incorporated in the formulation of the compound.

Compositions of the said invention may include certain anions and cations (e.g. alkyl metal chlorides) to facilitate penetration of the compound thru cell membranes. Non-limiting examples of anions include barbital, bicarbonate, borate, chloride, oxylate or EDTA. Not all anions have been found suitable for promoting penetration of cell membranes. Non-limiting examples of cations include sodium (as in sodium chloride), potassium (as in potassium chloride), trishydroxymethylamino methane (TRIS), tris [hydroxymethyl]-aminomethane-hydrochloric acid (TRIS-HCL), or triethanolamine (TEA).

Overall Advantages of Substituted Anthraquinone, Anthrapyrazole and Benzophenoxazine Probes:

The perceived brightness of a fluorochrome is determined by several intrinsic factors, including the fluorophore's molar extinction coefficient and quantum yield, as well as extrinsic factors such as the optical properties of the imaging setup (illumination wavelength and intensity, spectra of filters and dichroic mirrors), and the camera's sensitivity to the emission spectrum. A common misperception in the fluorescent probe industry is that fluorophores with the highest molar extinction coefficient and quantum yield provide superior performance. However, other factors should be considered as well when assessing overall performance of a fluorochrome in particular applications. For instance, despite relatively low quantum yield (QY=0.004) and modest molar extinction coefficient ($\epsilon$=45,000), anthraquinone-based fluorophores are actually superior to BODIPY and cyanine-based ones in live cell imaging applications when these other factors are taken into consideration. The dyes are highly resistant to photo-bleaching, display minimal concentration quenching upon sequestering in organelles, and possess excitation/emission profiles that are ideal for multiplexing with most commonly used fluorochromes. Far-red emitting anthraquinones can be excited by a wide range of convenient laser light wavelengths (488, 514, 568, 633 or 647 nm). The dye family's emission spectrum extends from 670 nm into the low infra-red region, providing minimal overlap with the emission spectra from UV and visible range dyes and photoproteins.

For example, GFP and the far red-emitting anthraquinone derivatives can be co-excited at 488 nm, generating clear spectral separation of the emission signals in live cells, and thus allowing live cell single-pass laser-scanning. This is an important factor in increasing throughput rate and permits live cell assays to track agonist/antagonist responses over time frames of minutes. In flow cytometry and laser scanning applications, far red-emitting substituted anthraquinones obviate the need for spectral compensation when used in conjunction with fluorescein or GFP-labeled probes.

Two-photon absorption can be used, in which two long wavelength photons, absorbed by the fluorochrome, promote it to an excited state that then emits a single photon of higher energy. This is an approach suitable for exciting intracellular or tissue samples at a wavelength that is more transparent to these media. The dependence of two-photon absorption on the intensity of the laser beam allows for high spatial selectivity by focusing the laser beam on the target cell and thus preventing any damage to adjacent cells. Relatively few dyes are suitable for practical experiments using two-photon excitation because most do not absorb two long wavelength photons efficiently, i.e., they have poor two-photon cross-sections. One issue with two-photon excitation experiments is that the emitted light is of a short wavelength compared to the excitation source, and this might not be in a convenient region to permeate out of cells of other tissues, and for detection. With the cited far-red emitting anthraquinones, however, two-photon excitation is possible beyond 1000 nm wavelengths. Also important relative to multi-color labeling applications is that the far red-emitting anthraquinones are two-photon dark for the Titanium-Sapphire laser range 700-850 nm wavelengths.

The far red-emitting fluorochromes, described herein, emit at wavelengths to which blood and tissue are relatively transparent. Since the fluorochromes will not absorb wavelengths that tissues absorb strongly, and do not have emission wavelengths that will be absorbed significantly by tissues, their signals are readily transmitted through tissues, allowing imaging of components within complex biological fluids, such as blood, as well as deeply within tissues, organs or even certain organisms.

Substituted Anthraquinone and Benzophenoxazine Probes for Multi-Parametric Analyses:

The invention relates to substituted anthraquinone and benzophenoxazine dyes suitable for use with a variety of imaging and detection instrumentation including, but not limited to, fluorimeters, spectrofluorimeters, fluorometric plate readers, flow cytometers, microarray readers, fluorescence microscopes, fluorescence imaging systems, fluorescence microvolume cell analysis instruments, robotic fluorescent colony pickers, capillary electrophoresis systems with fluorescence detectors, fluorescence-based lab-on-a chip devices or fluorescence-based microfluidic devices. Macroscopic, microscopic or nanoscopic imaging may be performed in conjunction with the compounds of the invention The described dyes may be applied to a wide variety of fluorescence-based detection and quantification strategies including, but not limited to, fluorescence lifetime imaging (FLI), fluorescence lifetime imaging microscopy (FLIM), Fluorescence lifetime imaging endoscopy (FLIE), fluorescence loss in photobleaching (FLIP), chromophore-assisted light inactivation (CALI), fluorescence resonance energy transfer (FRET), fluorescence recovery after photobleaching (FRAP), fluorescence recovery after photo-activation (FRAPa), fluorescence correlation spectroscopy (FCS), polarized fluorescence recovery after photobleaching (PFRAP), single-molecule fluorescence energy transfer (smFRET), fluorescence imaging with one nanometer accuracy (FIONA), single-molecule high-resolution colocalization (SHREC), super high resolution imaging with photobleaching (SHRIMP), total internal reflection fluorescence (TIRF), defocused orientation position imaging (DOPI), fluorescence photoactivation localization microscopy (FPALM), biplane FPALM (BP-FPALM), two-photon laser scanning fluorescence microscopy (2PLSM), three-photon laser scanning fluorescence microscopy (3PLSM), extended field laser confocal microscopy (EFLCM), time-gated luminescence (TGL), stimulated emission depletion (STED), large-area multiphoton laser scanning microscopy (LMLSM), three-dimensional structured illumination microscopy (3D-SIM), simultaneous spatial and temporal focusing (SSTF), spatially modulated illumination (SMI), Femtosecond Kerr-gated wide-field fluorescence microscopy, structured illumination wide-field fluorescence microscopy (SIWFFM), higher harmonic generation microscopy (HHGM), stochastic optical reconstruction microscopy (STORM), variable-angle epifluorescence microscopy (VAEM), multidirectional selective plane illumination microscopy (mSPIM), variable-angle total internal reflection fluorescence microscopy (VA-TIRFM), fluorescence microphotolysis (CFM), coherent anti-Stokes Raman scattering (CARS), fluorescence ratio imaging microscopy, time-correlated single-photon counting (TC-SPC), dynamic speckle illumination (DSI), standing wave total internal reflection fluorescence (SW-TIRF), reversible saturable/switchable optical transitions (RESOLFT), confocal and multiphoton laser scanning microscopy (CLSM), 4Pi microscopy, 1(5) microscopy, and spectrally resolved fluorescence lifetime imaging microscopy (SFLIM).

Examples of fluorochromes and fluorescent proteins that the new red and/or far-red emitting probes are spectrally compatible with in terms of multi-color imaging applications are summarized in table 2. Note that some of the fluorochromes listed in the table are cell-impermeable, but are often affixed to antibodies for cell surface-based multi-parametric live cell analysis.

TABLE 2

Commonly used fluorochromes in live cell imaging.

| Fluorochrome | Excitation maximum (nm) | Emission maximum (nm) |
|---|---|---|
| 5-Hydroxytryptamine (HAT) | 370-415 | 530 |
| Acridine orange | 500 | 526 |
| Acridine yellow | 470 | 550 |
| Alexa Fluor 532 | 530 | 555 |
| Alexa Fluor 546 | 554 | 570 |
| Alexafluor 488 | 494 | 519 |
| Blue Fluorescent Proteins (e.g. EBFP, EBFP2, Azurite, mKalama) | 383 | 445 |
| BODIPY-FL | 505 | 513 |
| Cascade Blue | 377 | 420 |
| Coelenterazine | 429 | 466 |
| Coumarin | 384 | 470 |
| Cyan Fluorescent Proteins (e.g. ECFP, Cerulean, CyPet, mCFP, AmCyan1, Midoriishi Cyan) | 435 | 475 |
| Cyanine 2 | 492 | 510 |
| Cyanine 3 | 550 | 570 |
| Cyanine 5 | 650 | 670 |
| Dansyl | 340 | 520 |
| DAPI | 358 | 461 |
| Erythrosin | 529 | 554 |
| Far-red Fluorescent Proteins (e.g. mPlum, AQ143) | 590 | 649 |
| FLUO 3 | 506 | 526 |
| Fluorescein | 495 | 525 |
| FURA 2 (ratiometric) | 362, 335 | 512, 505 |
| Green Fluorescent Proteins (e.g. EGFP, Emerald, aceGFP, TurboGFP, Azami Green, ZsGreen) | 490 | 509 |
| Hoechst 33258 or Hoechst 33342 | 352 | 461 |
| INDO 1 (ratiometric) | 349, 331 | 482, 398 |
| JC-1 (monomer, J-aggregate) | 510, 585 | 527, 590 |
| Lucifer Yellow | 488 | 550 |
| Nile Red | 485 | 525 |
| Oregon Green 488 | 493 | 520 |
| Propidium iodide | 305, 536 | 617 |
| QUIN 2 (ratiometric) | 354, 332 | 510, 505 |
| Red fluorescent proteins (e.g. mCherry, tdTomato, mStrawberry, J-Red, DsRed, Kusabira Orange, AsRed2, mRFP1, HcRed1, mRaspberry) | 570 | 590 |
| Rhodamine 110 | 496 | 520 |
| Rhodamine 123 | 505 | 534 |
| Rhodamine 6G | 525 | 555 |
| Rhodamine B | 540 | 625 |
| R-Phycoerythrin | 488 | 575 |
| R-Phycoerythrin-Texas Red | 480-565 | 615 |
| SNARF | 480 | 600/650 |
| Texas Red | 596 | 620 |
| UV-excitable Green Fluorescent Proteins (T-Sapphire) | 399 | 511 |
| Yellow fluorescent proteins (e.g. EYFP, Citrine, Venus, YPet, Topaz, PhiYFP, ZsYellow1, mBanana). | 516 | 530 |

Although linear unmixing systems should provide the ability to distinguish among large numbers of different fluorophores with partially overlapping spectra, it is possible, even with a simpler optical setup in wide-field microscopy, to clearly distinguish among four different fluorescent proteins along, with one of the substituted far red-emitting anthraquinone or benzophenoxazine dyes of the present invention. For instance, using appropriate filter sets, one may simultaneously image cyan, yellow, orange and red fluorescent proteins (Cerulean or CyPet, any YFP, morange or mKO and mCherry) along with any of the far-red emitting dye derivatives described in this application, with minimal spectral cross-talk. One possible filter set combination appropriate for performing such an experiment is summarized in Table 3.

TABLE 3

Possible filter set combination for 5-parameter imaging with various fluorescent proteins and an anthraquinone dye.

| Fluorochrome | Excitation filter (nm) | Emission filter (nm) |
|---|---|---|
| Cerulean or CyPet | 425/20 | 480/40 |
| mCitrine or YPet | 495/10 | 525/20 |
| mOrange or mKO | 545/10 | 575/25 |
| mCherry | 585/20 | 624/40 |
| Anthraquinone derivative | 628/40 | 695LP, 715LP or 780LP |

The described far red-emitting fluorochromes may also be used in conjunction with antibodies conjugated with various fluorochromes, such as fluorescein, R-phycoerythrin, and R-phycoerythrin-Texas Red, using a flow cytometer equipped with a single argon laser emitting 488-nm laser source. Despite this sub-optimal excitation wavelength, which results in more than a 20-fold reduction in peak fluorescence, the anthraquinones are concentrated and sequestered in organelles and sufficiently bright for the analysis. Suitable emission filter settings for performing this type of analysis are summarized in table 4. Fluorescence of the antigen staining would likely be collected in logarithmic mode and the anthraquinone staining in linear mode. No cell fixation step is required and no spectral compensation from either the emission spectra of R-phycoerythrin or R-phycoerythrin/Texas Red tandem conjugate is needed, because the particular anthraquinone derivatives emit in the far-red region of the spectrum.

TABLE 4

Possible emission filter set combination for 4-parameter flow cytometry measurements using various fluorescently-labeled antibodies and an anthraquinone dye.

| Fluorochrome | Emission filter (nm) |
|---|---|
| Fluorescein | 530/30 BP |
| R-Phycoerythrin | 585/42 BP |
| R-Phycoerythrin-Texas Red | 620/20 BP |
| Anthraquinone derivative | 675 LP |

Other anthraquinones, according to the invention, possess spectral properties that are analogous to mCherry, Texas Red or Nile Red dyes. These may be extensively multiplexed as well, for example substituting for mCherry in table 3 or R-phycoerythrin-Texas Red in table 4 and allowing addition of a far-red emitting dye, such as Draq-5, Alexafluor 660 conjugate, Alexafluor 680 conjugate, TOPRO-3, Spectrum FarRed or another far red-emitting anthraquinione or benzophenoxazine dye, as delineated by the present invention.

Detection and Isolation of Subcellular Organelles:

The preparation of samples for biochemical analysis of protein activity frequently requires cell lysis, followed by fractionation and purification of subcellular organelles. For instance, some apoptosis assays rely upon the isolation of cytosolic and mitochondrial cell fractions in order to monitor the release of cytochrome c from the mitochondria. In other assays, a nuclear fraction must be isolated in order to monitor translocation of steroid hormone receptors from the cytoplasm to the nucleus. In such assays, rapid isolation of the targeted organelle is crucial, especially when monitoring early biochemical events arising from the activation of cells. While many of these traditional biochemical assays are increasingly being displaced by imaging-based cell assays, detailed analysis of proteins at the molecular level, especially with respect to post-translational modifications and protein-ligand interactions, is particularly important to fields, such as proteomics and systems biology. Common methods for sub-cellular fractionation include density-gradient centrifugation, free flow electrophoresis, immuno-magnetic separation and field flow fractionation in microfabricated devices (Lab-on-chips). Once isolated, the desired fractions are typically identified based upon enrichment and specific activity of surrogate enzymes known to be localized to that organelle.

The various anthraquinone-, phenoxazine-, anthrapyrazole- and benzophenoxazine-based fluorochromes, alone or in combination with other fluorochromes and/or fluorescent proteins, provide a convenient tool for highlighting multiple organelles during their purification for enzyme assays, as well as, proteomics and systems biology applications, wherein multiple analyte profiling is subsequently performed. For instance, cells may be incubated with the anthraquinone in combination with Hoechst 33258 and JC-1 in order to label the lysosomal, nuclear and mitochondrial fractions, respectively. Cells are lysed and then subcellular fractions isolated using, for example, an 18 cm long, 1 mm wide, 50 μm deep microfabricated field flow fractionation device mounted to an inverted fluorescence microscope that is equipped with a digital camera. Roughly two volts is applied across the chamber and the lysed cells are introduced into the chamber of the device. Initially, the various organelles are distributed evenly throughout the chamber, as demonstrated by diffuse fluorescence through out, but as they flow through the chamber, the pH gradient develops and focusing of the various organelles occurs as demonstrated by the appearance of blue-red- and far red-emitting zones that represent nuclei, mitochondria and lysosomes, respectively. A fourth green-emitting zone is also usually observable, representing mitochondria stained with JC-1 monomer- (as opposed to J-aggregate), representing those mitochondria that have lost their transmembrane potential. Typically, 5-10 minutes is required in order to reach a steady state separation. The four zones may then be collected using a flow splitter at the end of the isoelectric focusing chamber, for further refinement of the separation process or for subsequent analysis by conventional enzymology, proteomics or systems biology approaches.

Other Applications

The novel dyes and compositions of the present invention can also be used in other applications. For instance, numerous molecules, such as DDAO-phosphate (7-hydroxy-9H-(1,3-dichloro-9,9-dimethylacridin-2-one phosphate) and difluorinated methylumbelliferyl phosphate (DiFMUP), are known to undergo changes in optical characteristics when one or more phosphate groups are removed. This removal and change serves as a basis for numerous phosphatase assays that have been described in the literature. Accordingly, in the present invention, the anthraquinones, the phenoxazines, the anthrapyrazoles and the benzophenoxazines may be synthesized with a phosphate moiety in an appropriate location of the molecule, thus making it useful and applicable in phosphatase activity measurement. Cell permeability may be facilitated through creation of phosphate esters, with regeneration of the phosphomonoester occurring after cell uptake, upon intracellular cleavage by endogenous esterases. Organelle-targeting of the anthraquinone phosphate ester, according to the present invention, permits localization of the substrate to regions of the cell where particular phosphatases or phosphatase family members reside. For example, lysosomal targeting is useful for measuring acid phosphatase activity, while plasma membrane targeting affords some measure of selectivity for protein tyrosine phosphatase 1B (PTP1B), which is known to negatively regulate EGF-induced signaling in several cell types by dephosphorylating the epidermal growth factor receptor (EGFR). Similar strategies can be employed to detect, localize or quantify β-glucuronidases, β-galactosidases, esterases, lipases, chitinase/N-acetylglucosaminidases or sulfatases, as nonlimiting examples.

In another embodiment of the present invention, the fluorescent capabilities of the anthraquinones, anthrapyrazoles and benzophenoxazines may also be used as labeling reagents where the presence of a reactive group on such molecules may allow their attachment to various targets. Such targets can include but not be limited to proteins and nucleic acids. These labeling reagents may also be part of oligomeric or polymeric complexes that may be used to attach multiple fluorescent molecules to a single site on targets such as proteins or nucleic acids, thereby providing tagged molecules with very high signal generating capability.

Reagent Kits:

Commercial kits are valuable because they eliminate the need for individual laboratories to optimize procedures, saving both time and resources. They also allow better cross-comparison of results generated from different laboratories. The present invention additionally provides reagent kits, i.e., reagent combinations or means, comprising all of the essential elements required to conduct a desired assay method. The reagent system is presented in a commercially packaged form, as a composition or admixture where the compatibility of the reagents will allow, in a test kit, i.e., a packaged combination of one or more containers, devices or the like holding the necessary reagents, and usually written instructions for the performance of the assays. Reagent systems of the present invention include all configurations and compositions for performing the various labeling and staining formats described herein.

The reagent system will generally comprise (1.) one or more substituted anthraquinone, anthrapyrazole or benzophenoxazine fluorochrome designed to target specific subcellular organelles, cell regions or cell domains. (2.) Instructions for usage of the included reagents. Generic instruction, as well as specific instructions for the use of the reagents on particular instruments, such as a wide-field microscope, confocal microscope, flow cytometer or microplate-based detection platform may be provided. Recommendations regarding filter sets and/or illumination sources for optimal performance of the reagents for a particular application may be provided.

A test kit form of the system for lysosomal labeling, for example, can contain one or more substituted anthraquinone, phenoxazines, anthrapyrazole or benzophenoxazine fluorochromes that localize to the lysosome, and additional ancillary chemicals, such as dilution buffer, live-cell DNA stain, live-cell mitochondrial stain and/or an antibody, a lectin, a $Ca^{2+}$-dependent, phospholipid binding protein (such as Annexin V), or other reporter labeled with a fluorophore. In some instances one or more fluorochrome may be combined within a single container for easier use. In some instances, calibrants are included, such as microsphere or bead standards of known fluorescent output.

Therapeutic Activity

The anthracycline doxorubicin, a DNA-targeting drug, is among the most versatile chemotherapeutic agents currently in clinical use. However, the proven clinical utility of doxorubicin has been tempered by dose-limiting cardiotoxicity, and this has prompted a search for analogs with comparable therapeutic efficacy, yet lacking the characteristic cardiotoxicity. Members of the anthracenedione class of compounds were identified as good drug candidates designed to satisfy these criteria. The anthracenediones, most notably mitoxantrone (Novatrone™) are simplified anthracycline analogues, which retain the planar ring structure characteristic of anthracyclines, permitting intercalation between base pairs of DNA.

Mitoxantrone (MTX) is an antineoplastic agent used in the treatment of certain types of cancer, mostly metastatic breast cancer, acute myeloid leukemia, and non-Hodgkin's lymphoma, as well as secondary progressive multiple sclerosis (MS). Without wishing to be bound by theory, it is believed that MTX displays cytotoxic activity when it poisons topoisomerase II by stabilizing the ternary, DNA-intercalator-Topo complex in such a way that the enzymatic process cannot continue forward or backward. The ternary complex is detected by the cell as a damaged portion, which triggers a series of events; one of the more important ones involving p53 protein, which induces cell apoptosis. Despite an improved clinical tolerability of MTX chemotherapy, it still exerts a range of toxic side-effects including myelosuppression and cardiotoxicity. One unfortunate side effect of the drug is that it undergoes redox cycling, giving rise to an accumulation of free radical species at the cardiac level.

MTX can be found as four intracellular species: nuclear MTX bound to DNA, MTX oxidative metabolite in endoplasmic reticulum, cytosolic MTX, and MTX in low polarity membranes. Only about 50% of the drug is actually associated with the nucleus and we believe it is the portion of the drug localized in the cytosolic compartments that leads to the generation of ROS, leading to cardiotoxicity. Drug metabolism and compartmentalization are key aspects of cell chemosensitization. Examples 25 and 26 demonstrate that the compounds described in this invention can have cytoxic or cytostatic activity in cancer cells. Better nuclear targeting of the carbocyclic anthraquinone core using compounds described in this invention will reduce cardiotoxicity and improve efficacy for this class of drugs. In general, improving the therapeutic profile of various drugs can be accomplished thru rational design that leads to better compartmentalization of the drug within the targeted region of the cell, and the compounds of this invention accomplish that goal. The fluorescence signature of the compounds is valuable in screening the compounds for their localization properties. While the principle is illustrated with DNA targeting antineoplastic agents, the same principle can be applied to other subcellular compartments, such as, for example, improving efficacy of mitochondriotoxic drugs. The potency and selectivity of drugs may be improved thru their selective targeting to different subcellular locations.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

EXAMPLE 1

Synthesis of 1,4-bis(2-(dimethylamino)ethylamino)-2,3-difluoro-5,8-dihydroxyanthracene-9,10-dione (Compound 1)

A mixture of 1,2,3,4-tetrafluoro-5,8-dihydroxyanthraquinone (1.0 g, 3.2 mmol) and N,N-dimethylethylenediamine (3 mL) in $CH_2Cl_2$ (30 mL) was stirred at room temperature for 12 hours. After evaporation of the solvents, the residue was purified by silica gel chromatography using isocratic solvent system of $EtOAc/MeOH/Et_3N$ (10:10:1) yielding 830 mgs of Compound 1 as dark blue product. Abs (max, PBS pH 7.4)=568 nm; Em=675 nm. The structure of Compound 1 is given below:

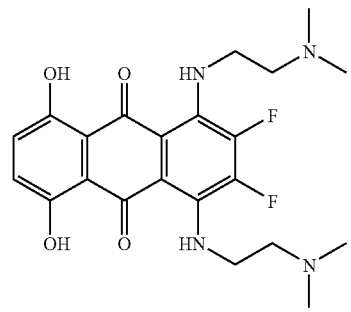 [SMILES: CN(C)CCNc1c(F)c(F)c(NCCN(C)C)c2c1C(=O)c1c(O)ccc(O)c1C2=O]

EXAMPLE 2

Synthesis of trifluoro-anthraquinone ceramide (Compound 2) and difluoro-anthraquinone ceramide (Compound 3)

A mixture of 1,2,3,4-tetrafluoro-5,8-dihydroxyanthraquinone ( 62.4 mg, 10.2 mmol), D-sphingosine(123 mg, 0.4 mmol) in $CH_2Cl_2$ (8 mL) was stirred at room temperature for 12 h. After evaporation of the solvents, the residue was purified on silica gel chromatography eluted with $EtOAc/MeOH/Et_3N$ (10:10:1) to afford monoamine substituted Compound 2 (115 mg) and diamine substituted Compound 3 (34 mg). Abs (max, PBS pH 7.4)=533 nm; Em=625 nm for Compound 2 and Abs (max, PBS pH 7.4)=572 nm; Em=697 nm for Compound 3. The structures of these compounds are given below:

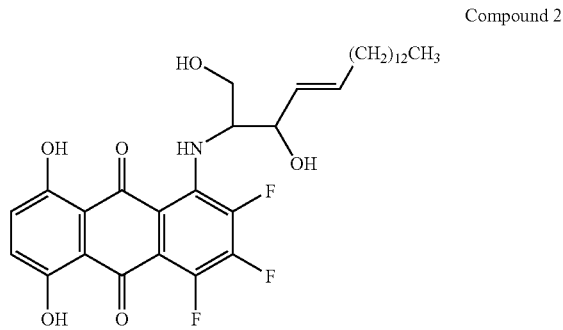

Compound 2

EXAMPLE 3

Synthesis of 1,2,3-trifluoro-5,8-dihydroxy-4-(2-(2-hydroxyethylamino)ethylamino)anthreacene-9,10-dione (Compound 4) and 2,3-difluoro-5,8-dihydroxyl,4-bis(2-(2-hydroxyethylamino) ethylamino) anthreacene-9,10-dione (Compound 5)

A mixture of 1,2,3,4-tetrafluoro-5,8-dihydroxyanthraquinone (1.0 g, 3.2 mmol) and 2-(2-aminoethylamino) ethanol (3.26 mL, 32 mmol) in CH$_2$Cl$_2$ (20 mL) was stirred at room temperature for 12 hours. After evaporation of the solvents, the residue was purified by silica gel chromatography using isocratic solvent system of EtOAc/MeOH/Et$_3$N (10:10:1) yielding 200 mg of Compound 4 and 350 mg of Compound 5. Abs (max, PBS pH 7.4)=593 nm for Compound 4 and Abs (max, PBS pH 7.4)=574 nm for Compound 5. The structures of these compounds are given below:

Compound 3
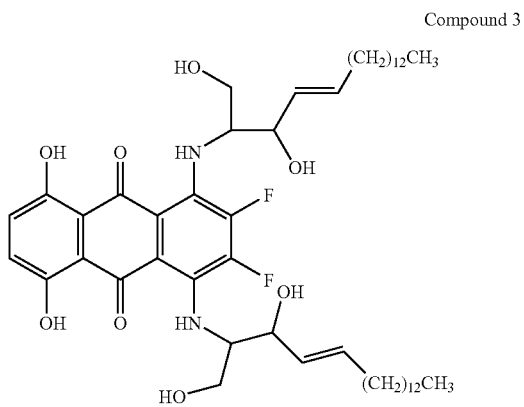

Compound 4
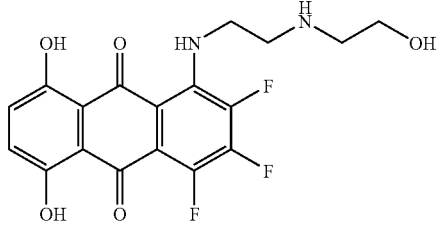

Compound 5
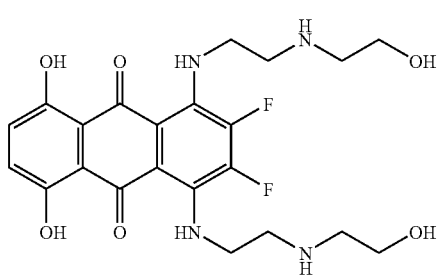

EXAMPLE 4

Synthesis of Compound 7 a) Preparation of 1,8-bis(2-(dimethylamino)ethylamino)anthracene-9,10-dione (Compound 6)

A mixture of 1,8-dichloroanthraquinone (5.5 g, 20 mmol) and N,N-dimethylethylenediamine (40 mL) was refluxed for 18 h. The mixture was cooled to room temperature and diluted with water to precipitate the title compound which was recrystallised from methanol to afford Compound 6 (4.5 g). The structure of Compound 6 is given below:

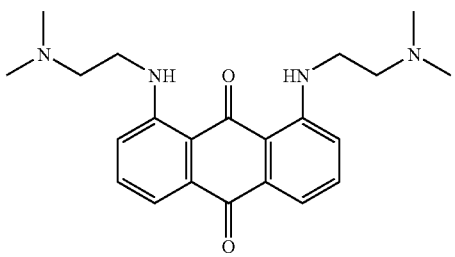

b) Preparation of 1,8-bis(2-(dimethylamino)ethylamino)-4,5-dihydroxyanthracene-9,10-dione (Compound 7)

The anthracene-9,10-dione derivative (Compound 6, 1.0 g, 2.6 mmol) was dissolved in 10 ml of concentrated H$_2$SO$_4$ and cooled to −10° C. Anhydrous sodium chlorate (1.1 g, 10.4 mmol) was added in portions over 1.5 h and the mixture then stirred for 12 h at room temperature. The blue solution was added slowly to a cold sodium hydrogen sulfite solution (1%, 160 mL). The mixture was neutralized to pH 7 with 5 M NaOH. The titled compound was extracted from the aqueous phrase with CH$_2$Cl$_2$ and concentrated in vacuum. Silica gel Column chromatography (CH$_2$Cl$_2$/MeOH: 9:1)gave Compound 7 (270 mg). Abs (max, PBS pH 7.4)=571 nm; Em=647 nm. The structure of Compound 7 is given below:

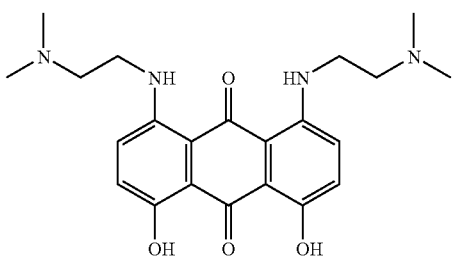

EXAMPLE 5

Synthesis of 1,1'-(dihydroxy-9,10-dioxo-9,10-dihydro anthracene-1,5-diyl)bis(3,3-dimethyl thiourea) (Compound 8)

A mixture of 1,5-diamino-4,8-dihydroxyanthraquinone (0.54 g, 2 mmols), Imidazole (1.34 g, 20 mmols), tert-butyldimethylsilyl chloride(0.66 g, 4.4 mmols) and 20 ml of MeCONMe$_2$) was heated at 120° C. for 2 hours. Dimethylthiocarbamoyl chloride (0.31 g, 2.5 mmols) was then added and the reaction mixture was stirred at 120° C. for another 2 hours. Upon cooling to room temperature, n-Bu4N+F (5 ml, 1M in THF) was added and the mixture was stirred for 1 hour. It was then concentrated in the rotary evaporator and purified by silica gel chromatography (5% of MeOH in $CH_2Cl_2$), yielding 60 mg of Compound 8 as a reddish soild. Abs (max, PBS pH 7.4)=629 nm; Em=669 nm. The structure of Compound 8 is given below:

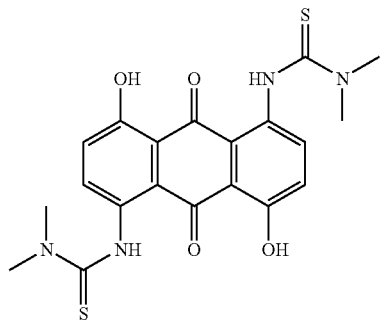

EXAMPLE 6

Synthesis of 1,5-bis((2-(dimethylamino)ethyl)(methyl)amino)anthracene-9,10-dione (Compound 9)

A mixture of 1,5-dichloroanthraquinone (5.5 g, 20 mmol) and N,N,N'-trimethylethylenediamine (40 ml) was refluxed for 18 h. The mixture was cooled to room temperature, diluted with water (400 mL) and extracted with chloroform (2×200 mL). The combined organic layer was washed with water, brine, dried over $MgSO_4$ and evaporated to dryness. The residue thus obtained was purified by silica gel flash chromatography [$CHCl_3$/MeOH/$Et_3N$ (44:5:1)] to provide Compound 9. Abs (max, PBS pH 7.4)=508 nm. The structure of Compound 9 is given below:

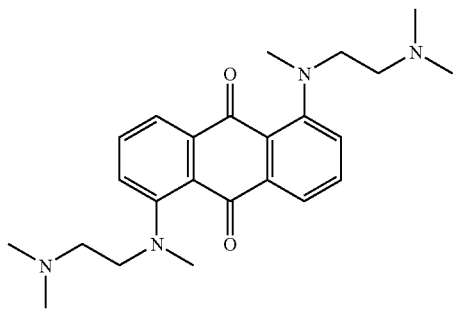

EXAMPLE 7

Synthesis of O,O'-4,8-bis(3,3-dimethylthioureido)-9,10-dioxo-9,10-dihydroanthracene-1,5-diyl bis(dimethyl carbamothioate) (Compound 10)

A mixture of 1,5-diamino-4,8-dihydroxyanthraquinone (0.54 g, 2 mmols), dimethylthiocarbamoyl chloride (1.5 g, 12 mmols), and 15 ml of MeCONMe$_2$ was heated at 100° C. overnight. The reaction mixture was concentrated and purified by silica gel chromatography eluted (3% of MeOH in $CH_2Cl_2$) to yield 320 mg of Compound 10. Abs (max, PBS pH 7.4)=516 nm; Em=613 nm. The structure of Compound 10 is given below:

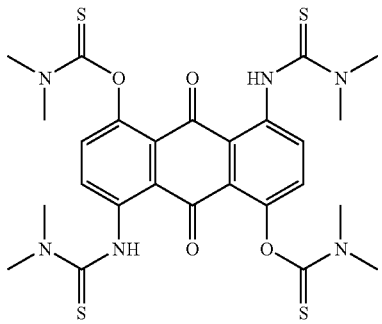

EXAMPLE 8

Synthesis of 1,5-bis(4-methylpiperazin-1-yl)anthracene-9,10-dione (Compound 11)

A mixture of 1,5-dichloroanthraquinone (4.00 g, 14.7 mmol) and 1-methylpiparazine (14.72 g, 147 mmol) was refluxed for 17 hours. The mixture was cooled to room temperature and diluted with water (100 mL) to precipitate the title compound. The brick red solid obtained was collected by filtration, washed with excess water and ether and dried under vacuum to afford 4.28 g of Compound 11. Abs (max, in water)=475 nm. The structure of Compound 11 is given below:

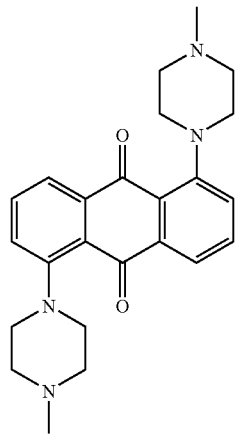 [SMILES: CN1CCN(c2cccc3c2C(=O)c2cccc(N4CCN(C)CC4)c2C3=O)CC1]

EXAMPLE 9

Synthesis of bis(2-dimethylamino) ethyl)3,3'-(4,8-dihydroxy-9,10-dioxo-9,10-dihydroanthracene-1,5-diyl) bis(azanediyl)dipropanoate (Compound 12)

A mixture of 1,5-diamino-4,8-dihydroxyanthraquinone (1.08 g, 4 mmols), 2-(dimethylamino)ethyl acrylate (1.52 ml, 10 mmols) and 10 mL of MeCONMe$_2$ was heated at 100° C. for 50 hours. The reaction mixture was concentrated and purified by silica gel chromatography (20% of MeOH in CH$_2$Cl$_2$), yielding 125 mg of Compound 12. Abs (max, PBS pH 7.4)=610 nm; Em=705 nm. The structure of Compound 12 is given below:

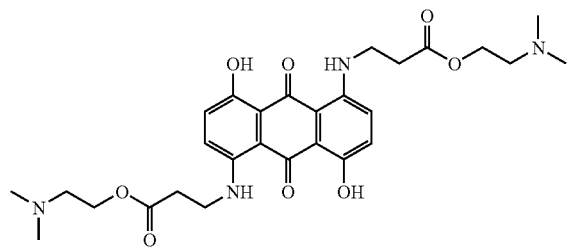

EXAMPLE 10

Synthesis of 1,5-bis(3-(diethyl phosphoryl)propylamino)-4,8-dihydroxyanthracene-9,10-dione (Compound 13)

A mixture of 1,5-diamino-4,8-dihydroxyanthraquinone (0.54 g, 2 mmols), Diethyl-(3-bromopropyl)phosphonate (1.15 ml, 6 mmols) and 15 ml of MeCONMe$_2$ was refluxed overnight. The reaction mixture was concentrated and purified by silica gel chromatography eluted with CH$_2$Cl$_2$ to yielding 420 mgs of compound x-v-53. Abs (max, PBS pH 7.4)=665 nm; Em=710 nm. The structure of Compound 13 is given below:

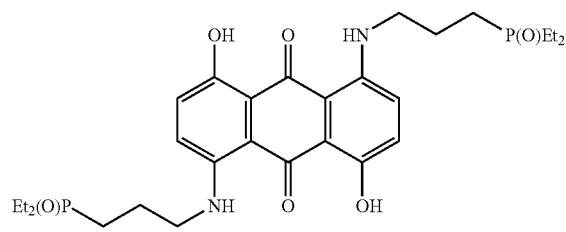

EXAMPLE 11

Synthesis of Compound 14

A mixture of 1,5-dichloroanthracene-9,10-dione (0.83 g, 3 mmol), dimethylaminoethylenehydrazine [which was prepared from dimethylaminoethylenehydrazine dihydrochloride(1.76 g, 10 mmol) and NaOH(0.4 g, 10 mmol) in 5 ml of H$_2$O] and MeCONMe$_2$ (15 mL) was refluxed for 12 hours. After evaporation of the solvents, the residue was purified by silica gel chromatography (10% MeOH in CH$_2$Cl$_2$) yielding Compound 14 (620 mg) as a yellow product. Abs (max, PBS pH 7.4)=415 nm; Em=498 nm. The structure of Compound 14 is given below:

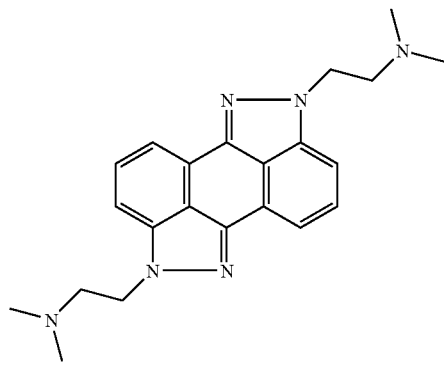

EXAMPLE 12

Synthesis of 1,5-bis(2-(dimethylamino)ethylamino) 4-nitroanthracene-9,10-dione (Compound 15) and 1,5-bis(2-(dimethylamino)ethylamino)4,8-dinitroanthracene-9,10-dione (Compound 16))

A solution of 1,5-bis(2-(dimethylamino)ethylamino)anthracene-9,10-dione (500 mg, 1.32 mmol) (prepared according to U.S. Pat. No. 6,468,753) in 8 mL of nitric acid (>90%) was heated at 40° C. for 3 h. The mixture was cooled to room temperature, diluted with 25 ml of water and neutralized to pH 7-8 with 5 N NaOH. The mixture was concentrated and purified on silica column chromatography (CH$_2$Cl$_2$/MeOH: 9:1)to afford Compound 15 (120 mg) and Compound 16 (52 mg). Abs (max, PBS pH 7.4)=586 nm for Compound 15 and 598 nm for Compound 16. The structure of Compounds 15 and 16 are given below:

Compound 15

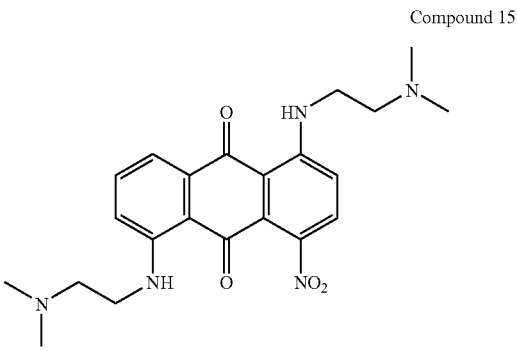

Compound 16

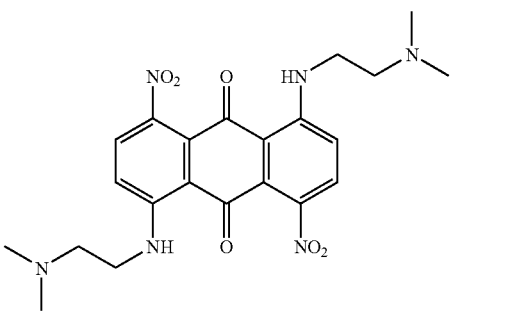

EXAMPLE 13

Synthesis of 1-(2-dimethylamino)ethylamino)-4-hydroxy-5-(4-methylpiperazin-1-yl)anthracene-9,10-dione (Compound 19)

a) Preparation of 1-Chloro-5-(2-(dimethylamino) ethylamino)anthracene-9,10-dione (Compound 17)

A mixture of 1,5-dichloro anthraquinone (5.0 g, 18.0 mmol), N,N-dimethylacetamide (30 mL) and N,N-dimethylethylenediamine (2 mL, 18 mmol) was stirred at room temperature for 1 hour and then heated in an oil bath (T=100° C.) for 45 minutes. Reaction mixture was cooled and filtered. To the filtrate petroleum ether (50 mL) was added and combined mixture was stirred at 4° C. over night. Precipitated solid was removed by filtration and supernatant was evaporated to dryness, co-evaporated with chloroform and dried under vacuum. The crude dye was then purified on Biotage SP4 system using a gradient of methanol in chloroform. Appropriate fractions were combined and evaporated to dryness to provide Compound 17 (1.0 g) as a red solid. Rf (9:1 CHCl$_3$/MeOH): 0.46; Abs (max, PBS)=500 nm. The structure of Compound 17 is given below:

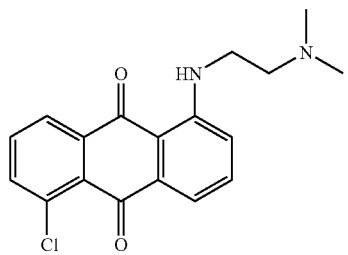 [SMILES: CN(C)CCNc1cccc2c1C(=O)c1cccc(Cl)c1C2=O]

b) Preparation of 1-(2-(dimethylamino)ethylamino)-5-(4-methylpiperazin-1-yl)anthracene-9,10-dione (Compound 18)

A mixture of Compound 17 (1.0 g, 3.0 mmol) and 1-methylpiparazine (1.5 g, 15.0 mmol) was refluxed for 17 hours. The mixture was cooled to room temperature, dissolved in 100 mL CH$_2$Cl$_2$ and extracted with water and brine. The organic layer was dried (Na$_2$SO$_4$) and evaporated to provide Compound 18 (540 mg). This product was used in the next step without any purification. Rf (9:1 CHCl3/MeOH): 0.15. The structure of Compound 18 is given below:

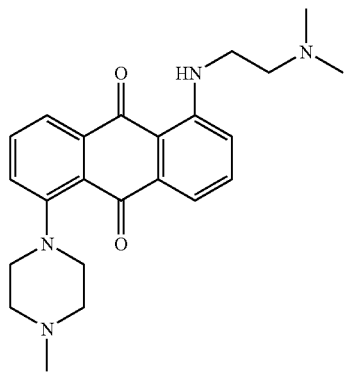 [SMILES: CN(C)CCNc1cccc2c1C(=O)c1cccc(N3CCN(C)CC3)c1C2=O]

c) Preparation of Compound 19

Compound 18 (0.54 g, 1.4 mmol) was dissolved in 4 mL of concentrated H$_2$SO$_4$ and cooled to −10° C. (ice/salt mixture). Anhydrous sodium chlorate (0.6 g, 5.6 mmol) was added in portions over 1.5 h and the mixture was stirred at room temperature for 22 h. The dark colored solution was added slowly to a cold sodium hydrogen sulfite solution (1%, 75 mL) and the mixture was neutralized to pH 7 with 10 M aqueous NaOH. The aqueous phase was extracted with CH$_2$Cl$_2$ (150 mL) and then the organic phase was washed with water, brine, dried (Na$_2$SO$_4$) and evaporated to dryness. The crude dye thus obtained was purified on Biotage SP4 system using a gradient of methanol in chloroform (7% to 60% over 10 column volume). Appropriate fractions were combined and evaporated to dryness to provide Compound 19 (50 mg) as a blue solid. R$_f$ (7:3 CHCl$_3$/MeOH): 0.31; Abs (max, PBS)= 525 and 600 nm; Em (max, PBS)=648 nm. The structure of Compound 19 is given below:

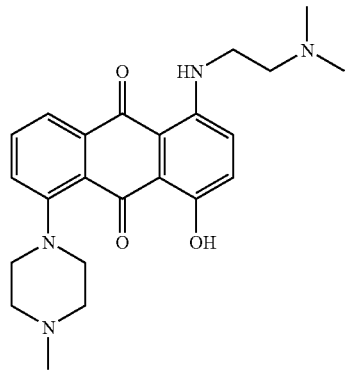 [SMILES: CN(C)CCNc1ccc(O)c2c1C(=O)c1cccc(N3CCN(C)CC3)c1C2=O]

EXAMPLE 14

Synthesis of 1,5-diamino-4,8-bis(2-(dimethylamino) ethyl amino)anthracene-9,10-dione (Compound 20)

A mixture of Compound 16 (25 mg) and concentrated HCl (2 ml) was cooled to 0° C. and then 50 mg of SnCl$_2$ was added. The combined mixture was stirred at 0° C. for 30 min and then warmed to room temperature for 5 hours. The mixture was then neutralized with 5 M NaOH and concentrated. The residue was purified by silica gel chromatography eluted (20% methanol in methylene chloride) to yield 15 mg of Compound 20. Abs (max, PBS pH 7.4)=690 nm. The structure of Compound 20 is given below:

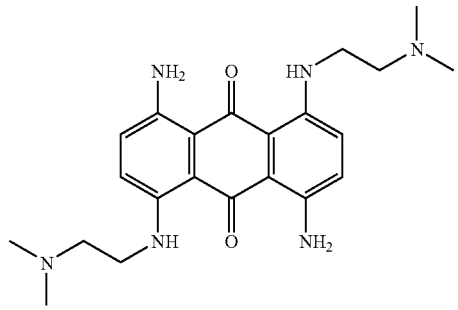

EXAMPLE 15

Synthesis of 1-(2-(dimethylamino) ethylamino4,8-dihydroxy-5-(2-hydroxy ethylamino)anthracene-9,10-dione (Compound 22)

a) Preparation of 1-(2-(dimethylamino)ethylamino)-5-(2-hydroxyl ethylamino)anthracene-9,10-dione (Compound 21)

A mixture of Compound 17 (0.87 g, 2.7 mmol) and ethanolamine (0.8 mL, 13.23 mmol) was heated in an oil bath (~150° C.) for 18 hours. The mixture was cooled to room temperature, dissolved in 100 mL $CH_2Cl_2$ and extracted with water and brine. The organic layer was dried ($Na_2SO_4$) and evaporated to provide Compound 21 (370 mg). This product was used in the next step without any purification. Rf (9:1 $CHCl_3$/MeOH) 0.19. The structure of Compound 21 is given below:

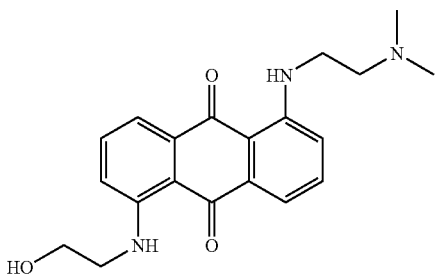 [SMILES: CN(C)CCNc1cccc2c1C(=O)c1cccc(NCCO)c1C2=O]

b) Preparation of Compound 22

This procedure was carried out as described previously in step (c) of Example 13, using Compound 21 (0.37 g, 1.05 mmol), $NaClO_3$ (0.45 g, 4.19 mmol) and conc $H_2SO_4$ (5 mL). The crude dye obtained was purified on Biotage (Flash 25+M) using a gradient of 2% to 20% methanol over 15 column volume. The dye was obtained as a blue solid (15 mg). The structure of Compound 22 is given below:

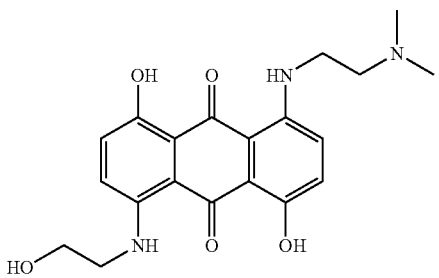 [SMILES: CN(C)CCNc1ccc(O)c2c1C(=O)c1c(O)ccc(NCCO)c1C2=O]

EXAMPLE 16

Synthesis of 1-(2-(dimethylamino) ethylamino-4,8-dihydroxy-5-(2-methoxy ethylamino)anthracene-9,10-dione (Compound 24)

a) Preparation of 1-(2-(dimethylamino) ethylamino-5-(2-methoxy ethylamino)anthracene-9,10-dione (Compound 23)

This procedure was carried out as described previously in step (a) of Example 15, using Compound 17 (0.25 g, 0.76 mmol) and 2-methoxyethylamin (0.66 mL, 7.6 mmol). This product was used in the next step without any purification. The structure of Compound 23 is given below:

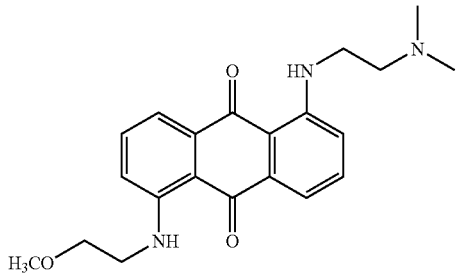 [SMILES: COCCNc1cccc2c1C(=O)c1cccc(NCCN(C)C)c1C2=O]

b) Preparation of Compound 24

This procedure was carried out as described previously in step (c) of Example 13, using Compound 23 (0.22 g, 0.61 mmol), $NaClO_3$ (0.26 g, 2.44 mmol) and conc $H_2SO_4$ (3 mL). The crude dye obtained was purified on Biotage (Flash 25+M) using a gradient of 2% to 20% methanol over 15 column volume. The dye was obtained as a blue solid (40 mg). The structure of Compound 24 is given below:

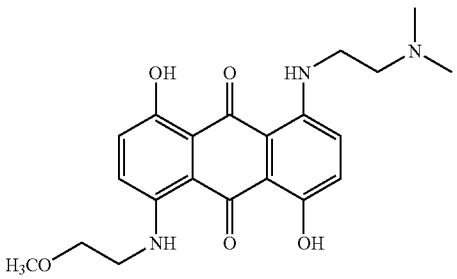 [SMILES: COCCNc1ccc(O)c2c1C(=O)c1c(O)ccc(NCCN(C)C)c1C2=O]

EXAMPLE 17

Synthesis of 1,5-dihydroxy-4,8-bis(2-methoxyethyl amino)anthracene-9,10-dione (Compound 26)

a) Preparation of 1,5-bis(2-methoxyethylamino)anthracene-9,10-dione (Compound 25)

This procedure was carried out as described previously in Example 8, using 1,5-dichloroanthraquinone (2.0 g, 7.22 mmol) and 2-methoxyethylamine (6.23 mL, 72.2 mmol). The dye was obtained as a red solid (2.39 g). The structure of Compound 26 is given below:

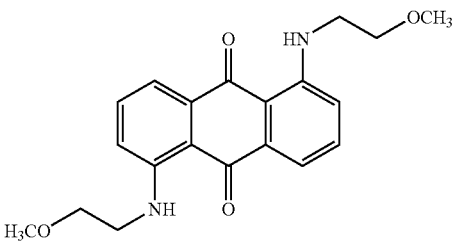 [SMILES: COCCNc1cccc2c1C(=O)c1cccc(NCCOC)c1C2=O]

b) Preparation of Compound 26

This procedure was carried out as described previously in step (c) of Example 13, using Compound 26 (0.5 g, 1.41 mmol), $NaClO_3$ (0.6 g, 5.64 mmol) and conc $H_2SO_4$ (5 mL). The crude dye obtained was purified by preparative TLC (hexane:ethyl acetate=1:1). The dye was obtained as a blue solid (9 mg). The structure of Compound 26 is given below:

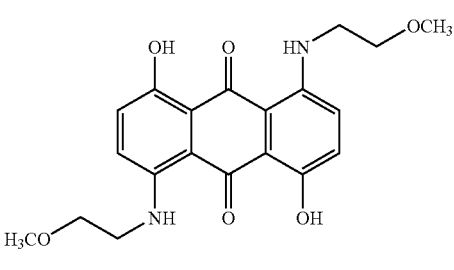 [SMILES: COCCNc1ccc(O)c2c1C(=O)c1c(O)ccc(NCCOC)c1C2=O]

EXAMPLE 18

Synthesis of 1,5-dihydroxy4,8-bis(pyridin-3-ylamino)anthracene-9,10-dione (Compound 28)

a) Preparation of 1,5-bis(pyridin-3-ylamino)anthracene-9,10-dione (Compound 27)

Potassium t-butoxide (3.37 g, 30 mmol) and $Pd_2(dba)_3$ (0.55 g, 0.6 mmol) were added to a 100 mL round bottom flask. Toluene (50 mL) and triisobutylphosphatrane (0.82 g, 2.4 mmol) were then added, followed by 3-aminopyridine (1.88 g, 20 mmol) and 1,5-dichloroanthraquinone (2.77 g, 10 mmol). The system was flushed with argon and heated to reflux overnight. The mixture was cooled and the solvent was removed under vacuum. The residue was dissolved in dichloromethane and water. The organic layer was washed with water twice and dried over anhydrous magnesium sulfate. After the solvent was removed, the residue was purified by flash chromatography to provide Compound 27 as a red solid. The structure of Compound 27 is given below:

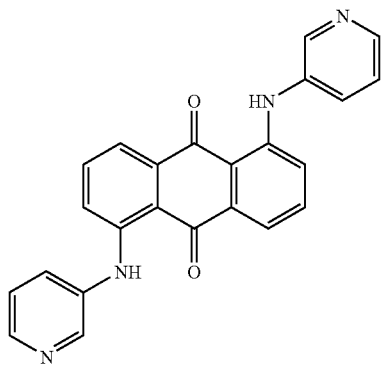 [SMILES: O=C1c2cccc(Nc3cccnc3)c2C(=O)c2cccc(Nc3cccnc3)c21]

b) Preparation of Compound 28

This procedure was carried out as described previously in step (c) of Example 13, using Compound 27 (0.4 g, 1.02 mmol), $NaClO_3$ (0.43 g, 4.07 mmol) and conc $H_2SO_4$ (3 mL). The crude dye obtained was purified by by flash chromatography. The dye was obtained as a blue solid (6 mg). The structure of Compound 28 is given below:

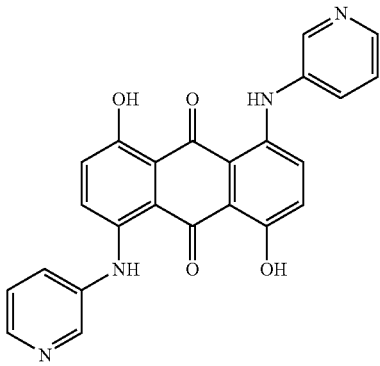 [SMILES: O=C1c2c(O)ccc(Nc3cccnc3)c2C(=O)c2c(O)ccc(Nc3cccnc3)c21]

EXAMPLE 19

Synthesis of 5,5'-(3,3'-oxy bis(ethane-2,2-diyl)bis(oxy))bis(propane-3,1-diyl)bis(1-(2-(dimethylamino) ethylamino)anthracene-9,10-dione) (Compound 29)

A mixture of Compound 17 (0.2 g, 0.61 mmol) and 4,7,10-trioxa-1,13-tridecane diamine (0.134 g, 134 μL, 0.61 mmol) was heated at 150° C. for 20 hours. The mixture was cooled to room temperature, dissolved in 10 mL $CHCl_3$ and purified on Biotage (Flash 25+M) using a gradient of 5% to 30% methanol in chloroform. The dye was obtained as a red solid (64 mg); Abs (max, PBS)=530 and 285 nm; Em (max, PBS)=655 nm. The structure of Compound 29 is given below:

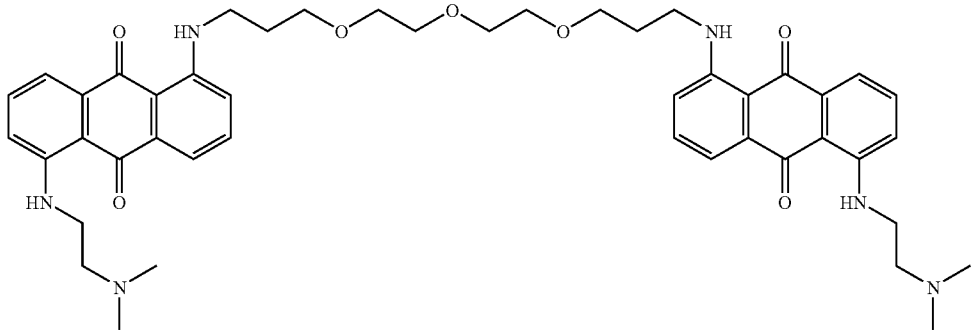 [SMILES: CN(C)CCNc1cccc2c1C(=O)c1cccc(NCCCOCCOCCOCCCNc3cccc4c3C(=O)c3cccc(NCCN(C)C)c3C4=O)c1C2=O]

EXAMPLE 20

Synthesis of 5,5'-(2,2'-oxybis(ethane-2,1-diyl)bis(azanediyl))bis(1-(2-(dimethylamino) ethylamino) anthracene-9,10-dione) (Compound 30)

This procedure was carried out as described previously in Example 19, using Compound 17 (187 mg, 0.57 mmol) and 2,2'-oxybis(ethylamine) (61 μL, 0.57 mmol). The dye was obtained as a red solid (50 mg) after Biotage purification using a gradient of methanol in chloroform. The structure of Compound 30 is given below:

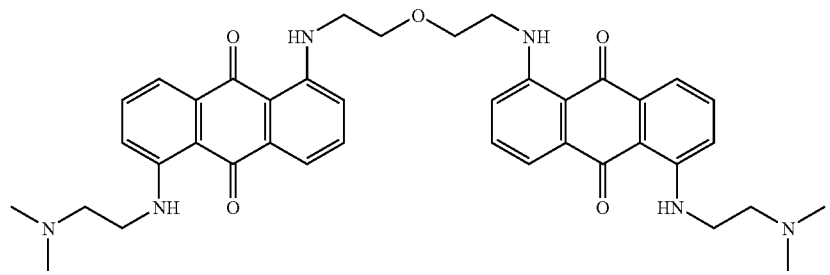

EXAMPLE 21

Synthesis of 5,5'-(2,2'-(methylazanediyl)bis(ethane-2,1-diyl)bis(azanediyl))bis(1-(2-(dimethylamino) ethylamino)anthracene-9,10-dione) (Compound 31)

This procedure was carried out as described previously in Example 19, using Compound 17 (545 mg, 1.66 mmol) and N-methyl-2,2'-diaminodiethylamine (214 µL, 1.66 mmol). The dye was obtained as a red solid (270 mg) after Biotage purification using a gradient of methanol in chloroform. The structure of Compound 31 is given below:

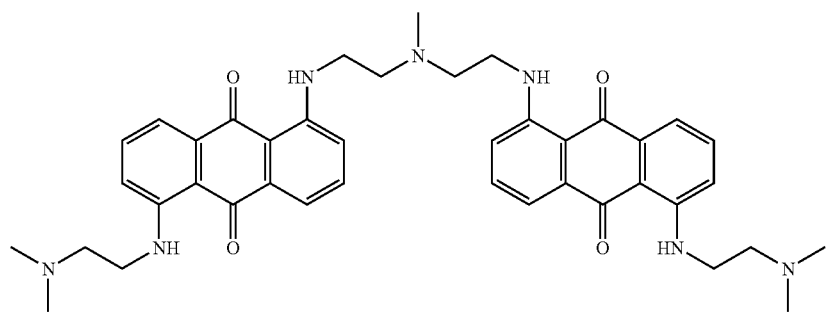

EXAMPLE 22

Synthesis of 8,8'-(2,2'-(methylazanediyl)bis(ethane-2,1-diyl)bis(azanediyl))bis(4-(2-(dimethylamino) ethylamino)-1,5-dihydroxyanthracen-9,10-dione) (Compound 32)

This procedure was carried out as described previously in step (c) of Example 13, using Compound 31 (0.27 g, 0.39 mmol), NaClO$_3$ (0.33 g, 3.1 mmol) and conc H$_2$SO$_4$ (6 mL). The crude dye obtained was purified on Biotage (Flash 25+M) using a gradient of 2% to 20% methanol over 15 column volume. The dye was obtained as a blue solid (25 mg). The structure of Compound 32 is given below:

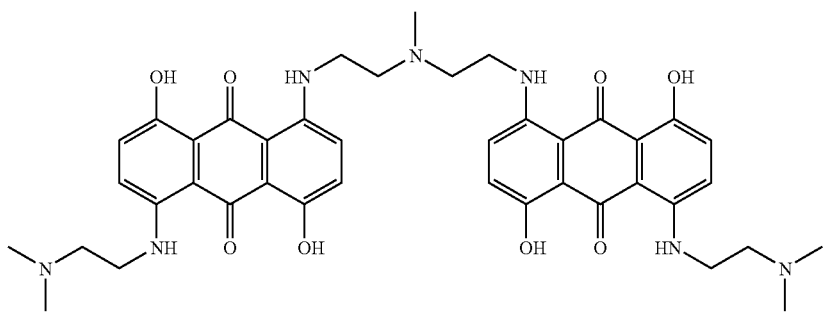

EXAMPLE 23

Synthesis of 5,5'-(3,3'-(methylazanediyl)bis(propane-3,1-diyl)bis(azanediyl))bis(1-(2-(dimethylamino)ethylamino)-anthracen-9,10-dione) (Compound 33)

This procedure was carried out as described previously in Example 19, using Compound 17 (520 mg, 1.58 mmol) and N,N-bis(3-aminopropyl) methylamine (383 µL, 2.37 mmol). The dye was obtained as a red solid (250 mg) after Biotage purification using a gradient of methanol in chloroform. The structure of Compound 33 is given below:

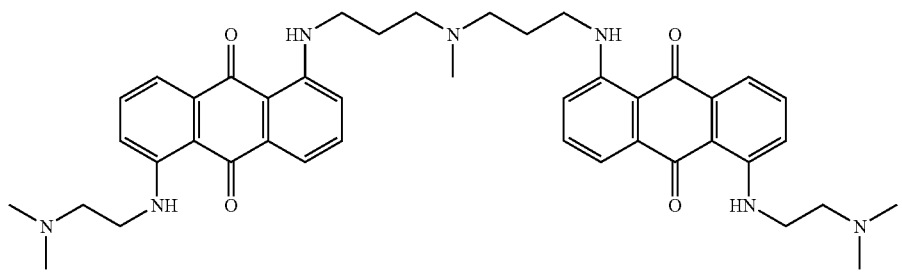

EXAMPLE 24

Staining of lysosomes in various live mammalian cells, using Compound 1

Cell cultures were maintained in an incubator at 37° C., with 5% $CO_2$ atmosphere. Human cervical adenocarcinoma epithelial cell line HeLa (ATTC, Manassas, Va.) was routinely cultured in Dulbecco's modified eagle medium with low Glucose (Sigma-Aldrich, St. Louis, Mo.), supplemented with 10% fetal bovine serum heat inactivated (Sigma), 0.25 ug/ml fungizone (Invitrogen Corp., Carlsbad, Calif.), 100 U/ml penicillin, 100 ug/ml streptomycin (Invitrogen) and 1% MEM Non-essential amino acids (Invitrogen). Chinese hamster ovary epithelial cell line CHO-K1 was obtained from ATCC. CHO-K1 cells were cultured in ATCC-formulated F12K medium supplemented with 10% fetal bovine serum heat inactivated (Sigma), 0.25 ug/ml fungizone (Invitrogen), 100 U/ml penicillin and 100 µg/ml streptomycin (Invitrogen). Human bone osteosarcoma epithelial cell line, U2-OS was obtained from ATCC and cells were cultured in McCoy's 5a medium ATCC-modified supplemented with 10% fetal bovine serum heat inactivated (Sigma), 0.25 ug/ml fungizone (Invitrogen), 100 U/ml penicillin and 100 ug/ml streptomycin (Invitrogen).

Compound 1 was dissolved in 0.005 N HCl to a 5 mM final stock concentration. For cell imaging, Compound 1 was added to culture media and cells were incubated for 15 min at ambient temperature or 37° C. in a cell culture incubator 5% $CO_2$ atmosphere. The media was removed and cells were washed 3 times with fresh medium. Cells were then imaged in phosphate-buffered saline (PBS) at ambient temperature. Imaging was performed using an Olympus BX51 microscope (60× objective). Exposure times were generally adjusted to around one sec. The microscope was equipped with Fluorescence Mirror units: set 41001 (Exciter: 480, Emitter: 535) for green detection (FITC); Set 41002c (Exciter: 545, Emitter: 620) for TRITC (Rhodamine with narrow-band excitation filter) red shifted emission; Filter set 41004 (Exciter 560, Emitter 645) for Texas Red emission; Set 41008 (Exciter: 620, Emitter 700,) for Cy5 emission. All filter sets were from Chroma Technology Corp, Rockingham, Vt.).

Figure 3:
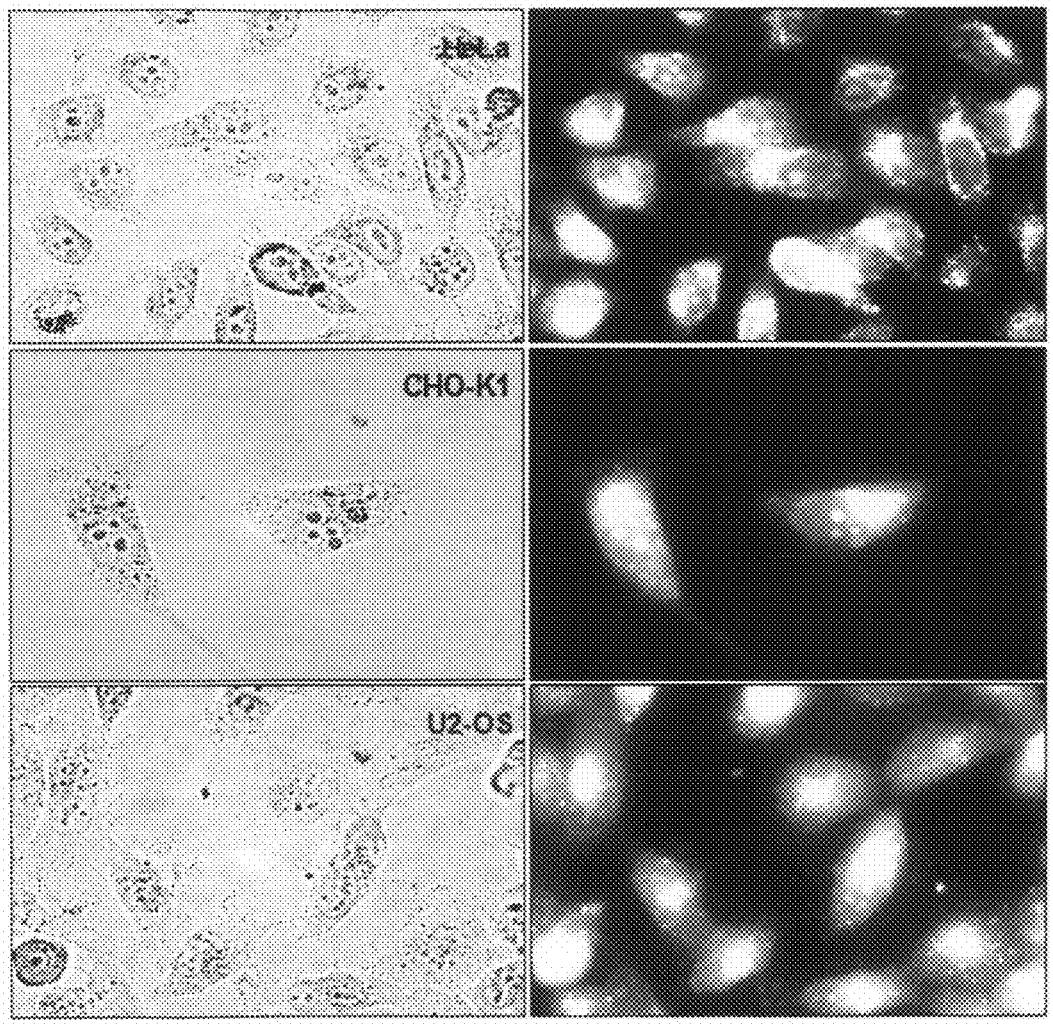
FIG. 3: Staining lysosomes in various live mammalian cells with an anthraquinone fluorochrome.

Titration of Compound 1 on Hela Cells indicated that 10 uM was the optimum concentration to stain lysosomes after 10 to 15 min incubation at room temperature or 37° C. As demonstrated in FIG. 3, Compound 1 localized to the lysosomes of all three cell lines evaluated. Similar experimental results were achieved using Compound 7.

EXAMPLE 25

Performance advantages of Compound 1 relative to Lysotracker Red DND-99 and acridine orange for the selective labeling of lysosomes in GFP-expressing cells.

Figure 4:
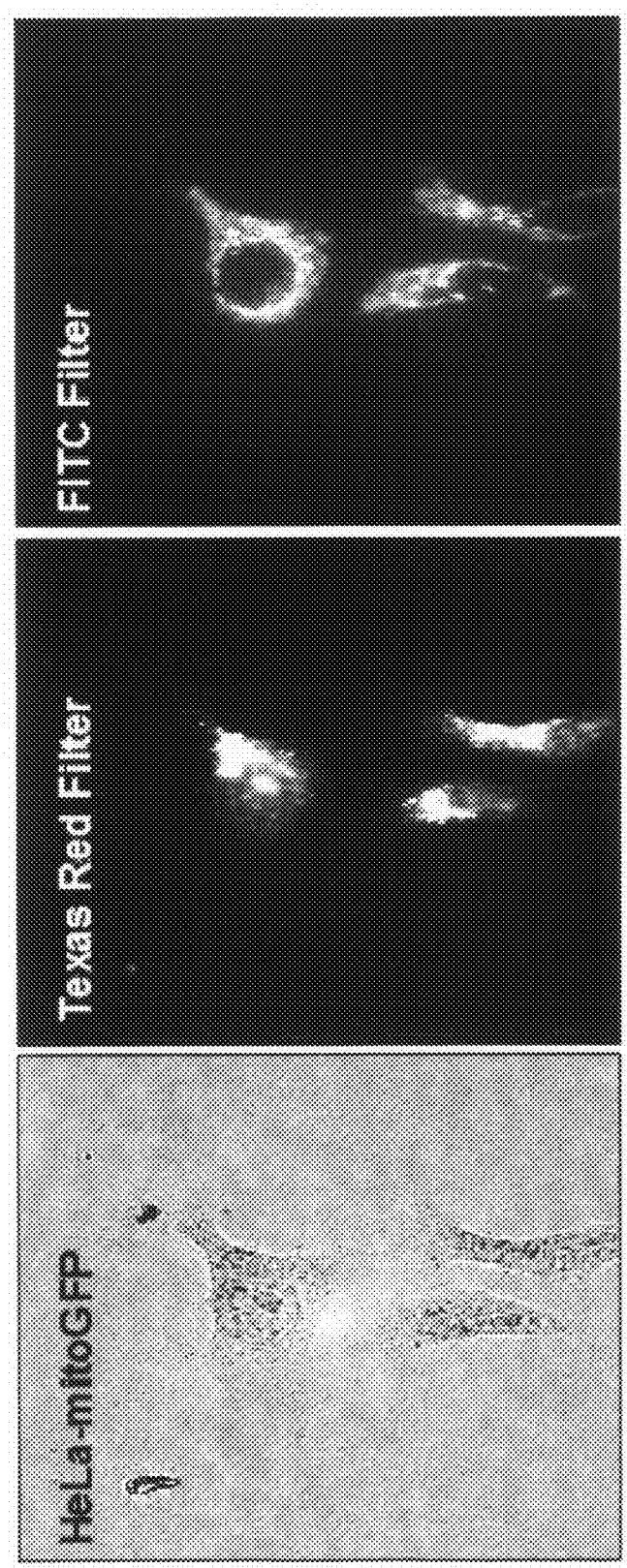
FIG. 4: Counter-staining lysosomes in GFP-expressing cells with an anthraquinone fluorochrome.

The HeLa-TurboGreen-mitochondria (HeLa-mitoGFP, MarinPharm GmbH, Luckenwalde, Germany) cell line expresses EGFP-cytochrome oxidase chimeric proteins that are primarily localized to the mitochondria. The cells were cultivated as described in Example 17 for standard HeLa cells. After incubation of these cells with compound 1, as described in example 17, lysosomes and mitochondria were independently imaged on an Olympus BX51 microscope (60x objective). Fluorescence signals from compound 1 and GFP were readily distinguished using the Texas Red and FITC filters, as shown in FIG. 4. Control HeLa cells, not expressing GFP, displayed no fluorescence signal in the FITC window, while HeLa-mitoGFP cells, not treated with Compound 1, displayed no fluorescence signal in the Texas Red window.

Figure 5A:
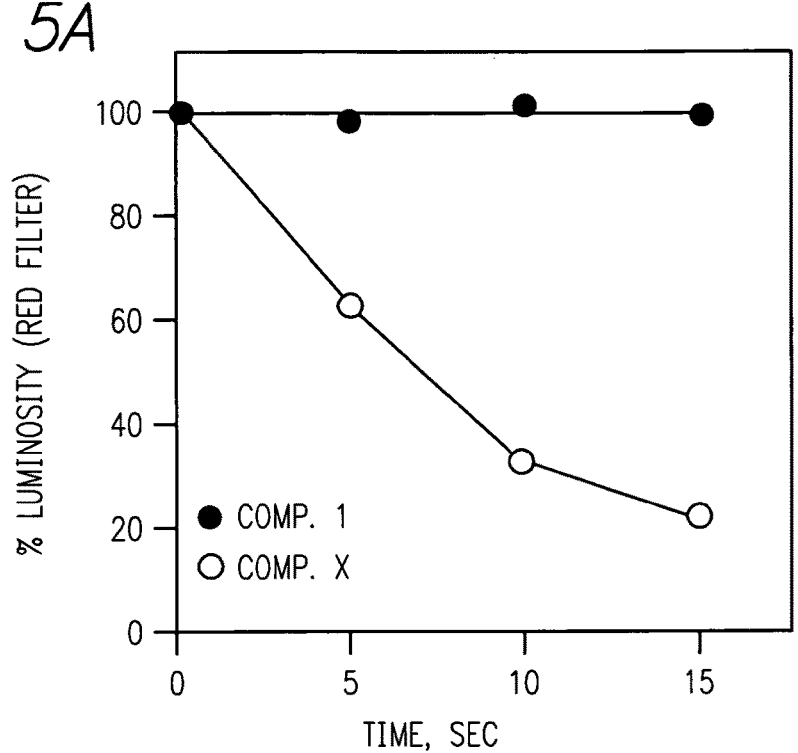
FIG. 5: Resistance of an anthraquinone fluorochrome to photo-bleaching and photo-conversion.
Figure 5B:
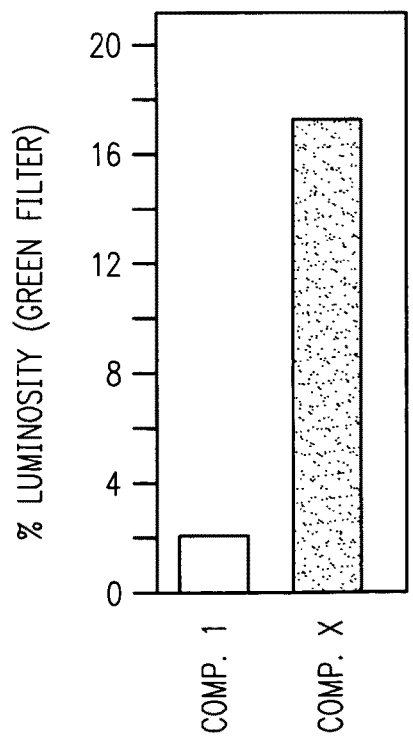

Despite long observation periods and long exposure times while imaging, the fluorescence of compound 1 does not fade away (FIG. 4, panel A). In contrast, LysoTracker Red rapidly photobleaches upon extended observation periods. Additionally, LysoTracker Red dye demonstrated photoconversion from a red to a green-emitting form, as previously reported (Freundt et al, 2007). This spurious signal was readily quantified in control HeLa cells and is depicted in FIG. 5b, relative to Compound 1.

Compound 1 is highly resistant to photobleaching relative to other dyes used for selectively labeling lysosomes. Compound 1 does not exhibit metachromasy, nor does it photoconvert to a green-emitting state, and is thus superior to acridine orange and Lysotracker Red for multi-color imaging in combination with GFP (Freundt et al, 2007; Nadrigny et al, 2007).

EXAMPLE 26

Staining of nuclei in various live mammalian cells, using Compound 11.

Figure 6:
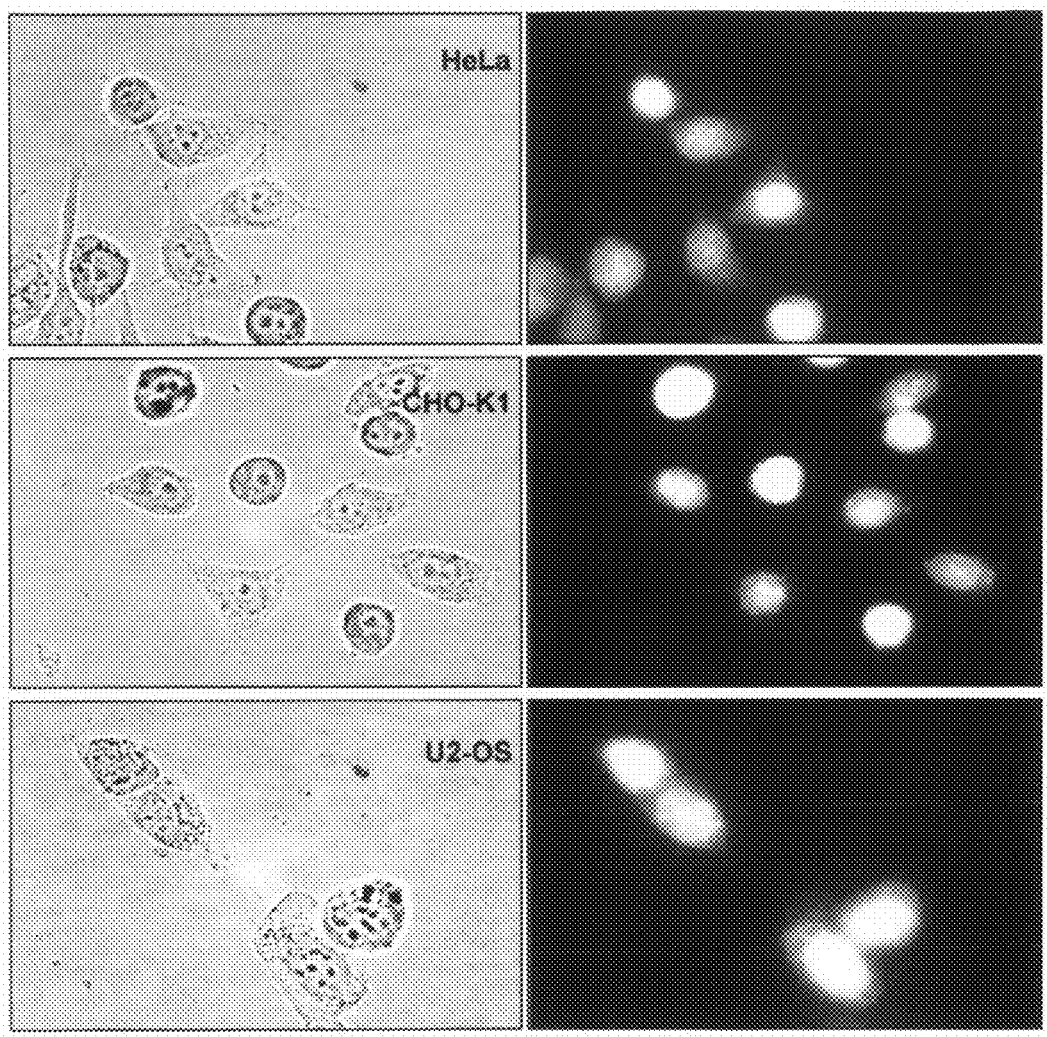
FIG. 6: Staining nuclei in various live mammalian cells with an anthraquinone fluorochrome.

The various mammalian cells were cultivated as described in example 17. After incubation of these cells with compound 11, as described in example 17, nuclei were imaged on an Olympus BX51 microscope (60× objective). CHO-K1 and U2-OS cells were incubated with various concentrations of Compound 11. At 100 µM some nuclear staining was observed, however 500 µM was optimum for staining nuclei after 15 min incubation at RT. As shown in FIG. 6, Compound 11 selectively accumulated on cell nuclei for all three mammalian cell lines evaluated. Similar experimental results were achieved using Compound 19. Lower concentrations of Compound 19 were required for staining of nuclei (10-20 µM) than for Compound 11 (~500 µM).

EXAMPLE 27

Staining of nuclei with compound 11 in GFP-expressing cells.

Figure 7:
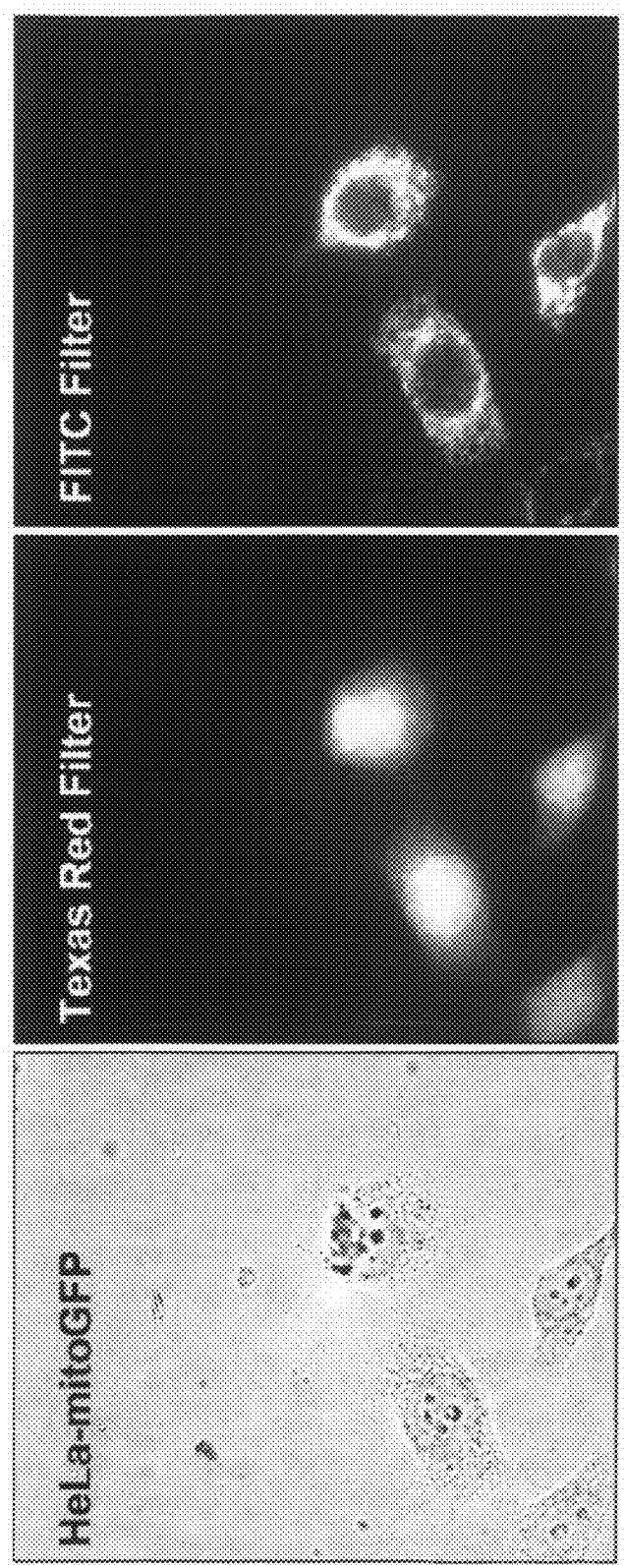
FIG. 7: Counter-staining nuclei in GFP-expressing cells with an anthraquinone fluorochrome.

The HeLa-TurboGreen-mitochondria (HeLa-mitoGFP, MarinPharm GmbH, Luckenwalde, Germany) cell line expresses EGFP-cytochrome oxidase chimeric proteins that are primarily localized to the mitochondria. The cells were cultivated as described in Example 12 for standard HeLa cells. After incubation of these cells with Compound 11, as described in Example 14, nuclei and mitochondria were independently imaged on an Olympus BX51 microscope (60x objective). Fluorescence signals from Compound 11 and GFP were readily distinguished using the Texas Red and FITC filters, as shown in FIG. 7. Control HeLa cells, not expressing GFP, displayed no fluorescence signal in the FITC window, while HeLa-mitoGFP cells, not treated with Compound 1, displayed no fluorescence signal in the Texas Red window. As with Compound 1, Compound 11 was not susceptible to photo-conversion to a green-emitting compound and exhibited excellent photostability relative to other commercially available nuclear stains. Additionally, the phostostability was comparable to the anthraquinone-based dye, DRAQ5 (Biostatus Limited, Coventry, England).

EXAMPLE 28

Simultaneous detection of nuclei, lysosomes and mitochondria using compound 1 and Hoechst 33342 dye in live GFP-expressing mammalian cells.

One fundamental aspect of both flow cytometry and fluorescence microscopy is their ability to analyze and compare multiple cellular parameters simultaneously. In many instances, this requires that multiple dyes be loaded into a given set of cells. An important assumption in this type of work is that the various dyes do not interact with one another. However, previous efforts to simultaneously visualize nuclei and lysosomes in living cells has been compromised by observed incompatibilities between Draq5 and the Lysotracker family of dyes (Lysotracker Green DND 26 and Lysotracker Red DND 99, Invitrogen Corporation) (Snyder and Garon, 2003). When co-incubated with cells, the Draq5 nuclear stain almost completely inhibits uptake of the BODIPY dyes, possibly due to the two dyes complexing in solution into a form that is not taken up by cells. BODIPY-mycolactone is a fluorescent adduct of the macrolide produced by Mycobacterium ulcerans, a molecule known to localize to the cytoplasm of cells. Its entry into cells is also blocked by Draq5, suggesting that any BODIPY-based probe would be susceptible to this phenomenon. Although it would seem a simple matter to circumvent the observed dye interaction by adding the compounds sequentially with washing between steps, this too has led to problems. Regardless of whether the Lysotracker dye is incubated with cells prior to or after Draq5 labeling, minimal lysosomal labeling is observed.

Figure 8:
FIG. 8: Counter-staining lysosomes and nuclei in GFP-expressing cells with an anthraquinone fluorochrome and Hoechst 33258.

In order to achieve simultaneous labeling of nuclear, mitochondrial and lysosomal compartments in live cells, Compound 1 was prepared in combination with Hoechst 33342. The HeLa-TurboGreen-mitochondria (HeLa-mitoGFP, MarinPharm GmbH, Luckenwalde, Germany) cell line expresses EGFP-cytochrome oxidase chimeric proteins that are primarily localized to the mitochondria. The cells were cultivated as described in Example 12 for standard HeLa cells. After incubation of these cells with a mixture of Compound 1 and Hoechst 33342, nuclei, lysosomes and mitochondria were independently imaged on an Olympus BX51 microscope (60× objective). Fluorescence signals from Compound 1, GFP and Hoechst 33342 were readily distinguished using the Texas Red, FITC and DAPI filters, as shown in FIG. 8. No adverse interaction between Compound 1 and Hoechst 33342 dye was noted.

EXAMPLE 29

Cytotoxicity of compounds 10, 11 and 19 toward HeLa human cervical adenocarcinoma cell line.

Human cervical adenocarcinoma epithelial cell line HeLa was obtained from ATCC (ATTC, Manassas, Va.) and was routinely cultured in Dulbecco's modified eagle medium with low Glucose (Sigma-Aldrich, St. Louis, Mo.), supplemented with 10% fetal bovine serum heat inactivated (ATCC) and 100 U/ml penicillin, 100 µg/ml streptomycin (Sigma). Cell cultures were maintained in an incubator at 37° C., with 5% $CO_2$ atmosphere. Compound 10 was dissolved in DMSO to a 5 mM final stock concentration. Compound 11 was dissolved in 0.02 N HCl to a 20 mM final stock concentration. Compound 19 was dissolved in PBS to a 1 mM final stock concentration. Cytotoxicity of compounds 10, 11 and 19 was determined using standard MTT (3-(4,5-dimethyl-2-thiazolyl)-2, 5-diphenyl-2H tetrazolium bromide) assay. The MTT assay is a laboratory test and a standard colorimetric assay (an assay which measures changes in color) for measuring the activity of enzymes that reduce MTT to formazan, giving a purple color. This mostly happens in mitochondria, and as such it is a measure of mitochondrial activity. The assay is typically used to determine cytotoxicity of potential medicinal agents and toxic materials.

For the cytotoxicity assay, HeLa cells were seeded in a 96 well plate at different densities ($10^3$, $5 \times 10^3$ and $10^4$ per well) and the next day were treated with serial dilutions of compounds 10, 11 or 19 in growth medium. Serial dilutions of compounds 10 and 11 were made in a range from 0.3 µM to 20 µM, compound 19 was tested in a range from 0.08 µM to 5 µM. Cells were incubated at 37° C. in a cell culture incubator 5% $CO_2$ atmosphere. The MTT assay was performed on day 1, 4 and 6 post treatment (for low cell density plates, $10^3$ cells/well) and on day 1 for plates with high cell density ($5 \times 10^3$ and $10^4$ per well). Growth media containing tested compounds was removed and 100 µL of fresh medium containing 0.5 mg/ml of MTT reagent was added to each well. Cells were incubated at 37° C. in a cell culture incubator 5% $CO_2$ atmosphere for 4 h, then 100 µL of solubilization solution (0.1N HCl in 10% SDS) was added to each well. After complete solubilization of the violet crystals (checked by microscope), optical density was read at 590 nm and cell viability was determined as a ratio of optical density of treated cells to optical density of untreated cells.

Figure 9:
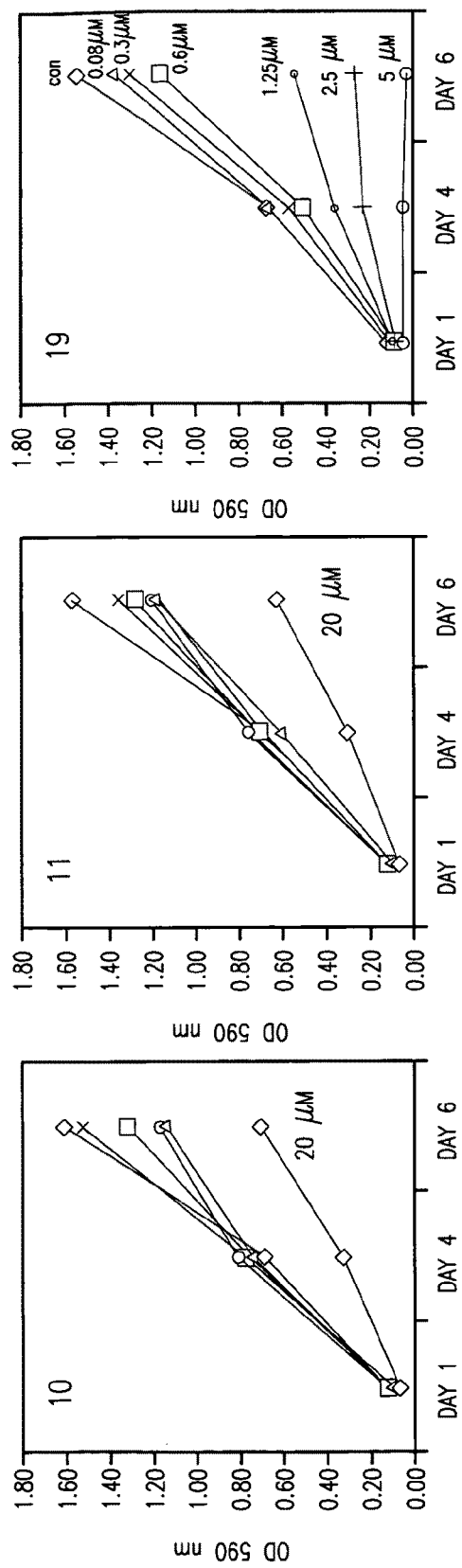
FIG. 9: Growth curves of HeLa cells treated with serial dilutions of anthraquinone-derived compounds.
Figure 10B:
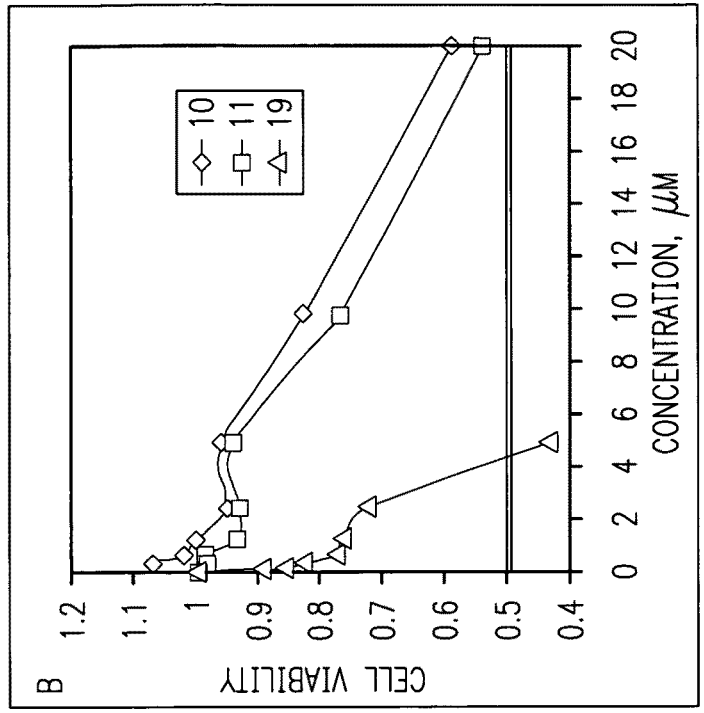
FIG. 10: Viability of the HeLa cells seeded at low and high density and treated with serial dilutions of anthraquinone-derived compounds.
Figure 10A:
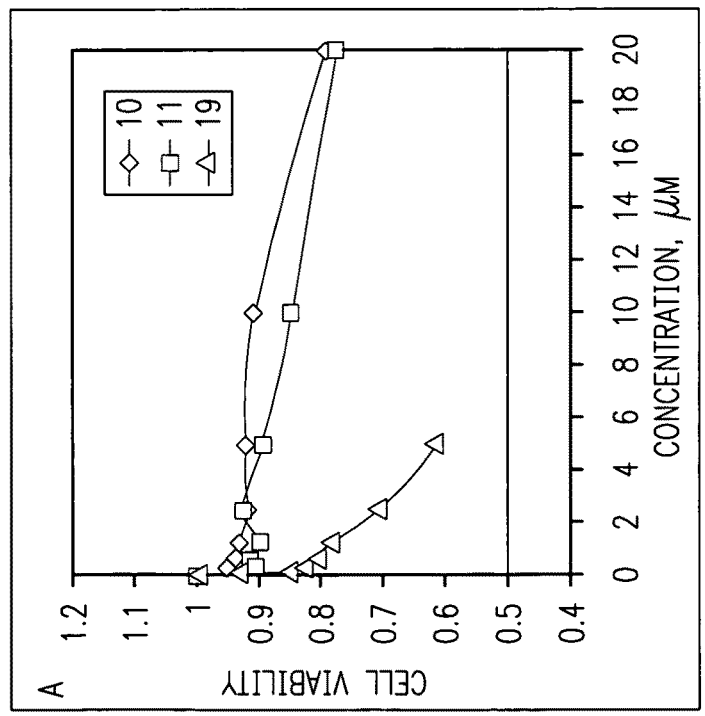

As demonstrated in FIG. 9, Compound 19 turned out to be the most cytotoxic of the three tested derivatives. For a 24 h incubation period, an IC50 of 5 µM for this compound was determined on low density HeLa cells. Two other compounds, 10 and 11, did not kill 50% of the cells during the 24 h period at concentrations tested. Experiments with HeLa cells seeded at low density were extended up to 6 days of treatment. Results of the extended experiment are presented in FIG. 10. Compound 10 and 11 exhibit slight concentration dependent growth suppressive effects (at concentrations higher than 5 µM). Only the highest concentration of compounds 10 and 11 (20 µM) had a significant growth suppressive effect on HeLa cells. However, HeLa cells treated even with the highest concentration of the compounds continue to grow. Over extended periods of time, compound 19 demonstrated a strong dose-dependent cytotoxic effect, and cells treated with this compound do not re-grow.

EXAMPLE 30

Mitochondrial and nuclear localized anthraquinone-based compounds 10,11 and 19 induced apoptosis in HeLa human cervical carcinoma cell line.

Figure 11:
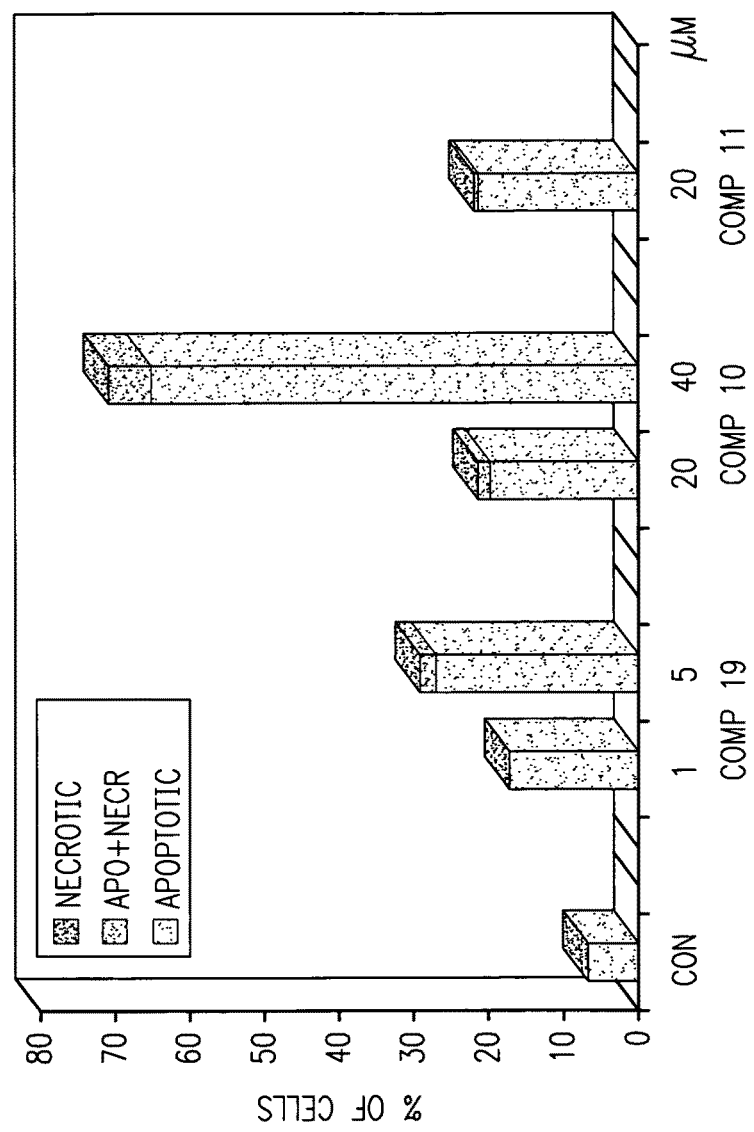
FIG. 11: Apoptosis induction in HeLa cells treated with anthraquinone-derived compounds.

The human cervical adenocarcinoma HeLa cells were cultivated as described in example 25. An annexin V binding assay was utilized to detect apoptosis induction by anthraquinone-derived compounds 10, 11 and 19. The day before the experiment, HeLa cells were seeded in 6-well tissue culture plates at a density of $5 \times 10^6$ cells per well. The next day, the growth medium was removed from the wells and fresh medium containing different dilutions of compounds 10 (20 and 40 µM), 11 (20 µM) and 19 (1 and 5 µM) was added. Cells were incubated for three h in the cell culture incubator at 37° C. and 5% $CO_2$, washed with PBS, trypsinized, again washed twice with PBS and stained with Annexin V-FITC conjugate (Invitrogen, Carlsbad, Calif.) according to the manufacturer's instructions and analyzed using flow cytometry. To assess the cell membrane permeability, cells were counterstained with 10 µg/ml of 7-AAD just before the assay. FITC fluorescence was recorded in FL1 channel (filter 530/30 nm) and 7-AAD fluorescence was recorded in FL3 channel (670 LP filter). Cell debris were gated out and apoptosis was assessed by setting up quadrant gates using untreated cells as a control. Depending upon concentration, all tested compounds induced apoptosis in HeLa cells after 3 h treatment (FIG. 11). However, the range of apoptosis-inducing concentrations is much lower for compound 19. All tested compounds appeared to induce cell growth arrest at low concentrations, and apoptosis at higher concentrations, however the threshold for apoptosis induction is different for different compounds.

EXAMPLE 31

Synthesis of 1-((2-(dimethylamino)ethyl) (methyl) amino)-5-(2-(dimethylamino) ethylamino)anthracene-9,10-dione (Compound 41)

This procedure was carried out as described previously in Example 19, using Compound 17 (500 mg, 1.52 mmol) and N,N,N'-trimethylethylenediamine (988 µL, 7.6 mmol). The dye was obtained as a red solid (260 mg) after Biotage purification using a gradient of methanol in chloroform. Abs (max, PBS pH 7.4)=530 nm; Em=646 nm. The structure of Compound 41 is given below:

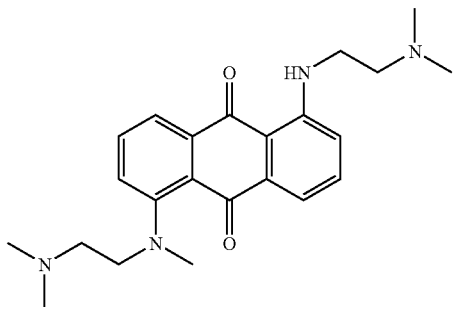

EXAMPLE 32

Synthesis of 1,5-bis(2-(dimethylamino) ethylamino)-4-hydroxy anthracene-9,10-dione (Compound 43)

This procedure was carried out as described previously in step (c) of Example 13 using Compound 17 (0.35 g, 1.1 mmol), $NaClO_3$ (0.47 g, 4.43 mmol) and conc. $H_2SO_4$ (5 mL). The crude dye obtained was purified on Biotage (Flash 25+M) using a gradient of 0% to 10% methanol over 15 column volume. The dye was obtained as a purple solid which was then refluxed with 2 mL of N,N-dimethylethylenediamine in dimethylacetamide (5 mL) for 18 hours. Compound 43 was purified by preparative TLC and was obtained as a purple solid (4.5 mg). The structure of Compound 43 is given below:

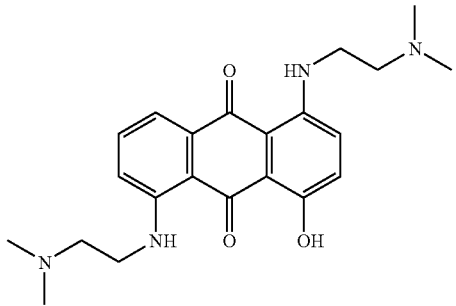

EXAMPLE 33

Excitation and Emission data for Compound 43 and DRAQ5:

Compound 43 and Draq5 were diluted to 100 µM in PBS. Using a Photon Technology International fluorescence spectrophotometer, both an emission and an excitation spectrum were taken for each compound. The excitation scan used the previously determined emission maximum for the emission and scanned at 1 nm intervals from 500 nm up to 5 nm below the emission maximum. The emission scans used the previously determined excitation maximum wavelength, and scanned the emission from 5 nm above the excitation wavelength to 700 nm for compound 43, and 750 nM for Draq5.

TABLE 5

Comparison of excitation and emission data for Compound 43 and DRAQ5.

| Dye | λmax (Excitation, nm) | λmax (Emission, nm) |
|---|---|---|
| Compound 43 | 563 | 634 |
| DRAQ5 | 644 | 678 |

EXAMPLE 34

Images in the red (TxRed) and far-red (Cy5) channel for Compound 43 and DRAQ5.

Figure 13:
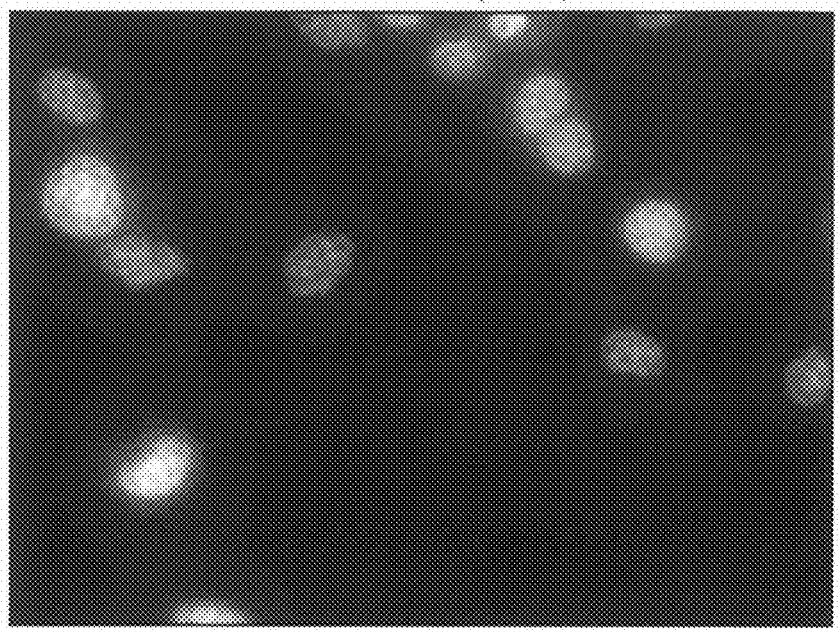
FIG. 13: Images in the red (Texas Red) and far red (Cy5) channel for Compound 43.
Figure 13:
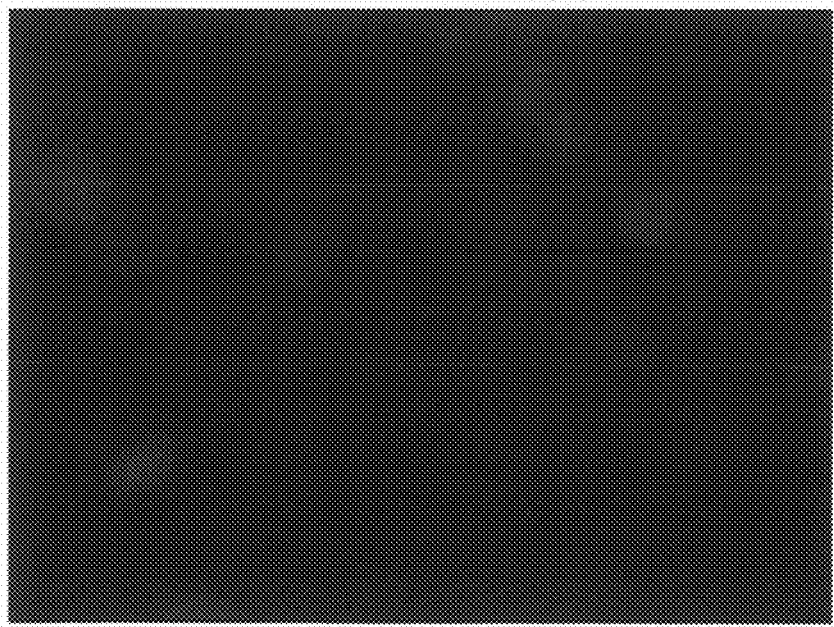
Figure 14:
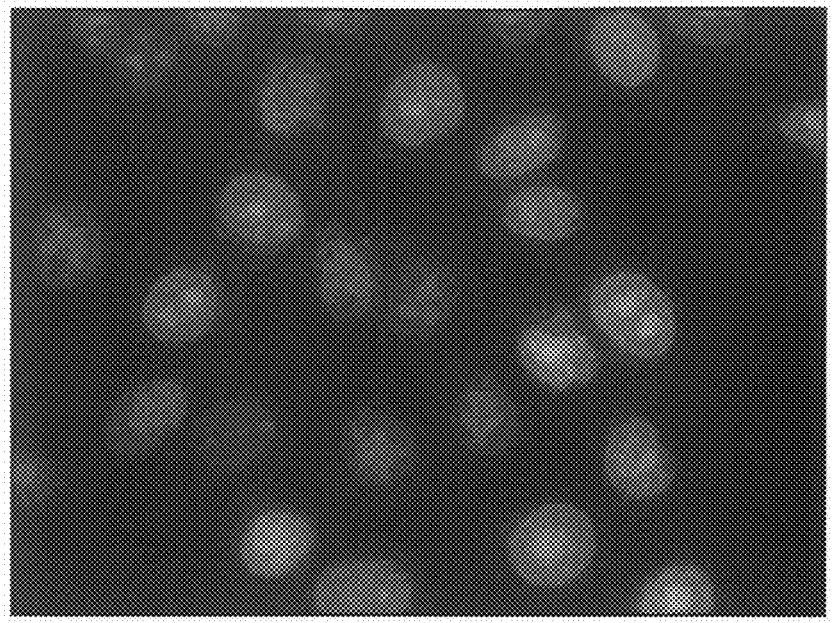
FIG. 14: Images in the red (Texas Red) and far red (Cy5) channel for Draq5 compound.
Figure 14:
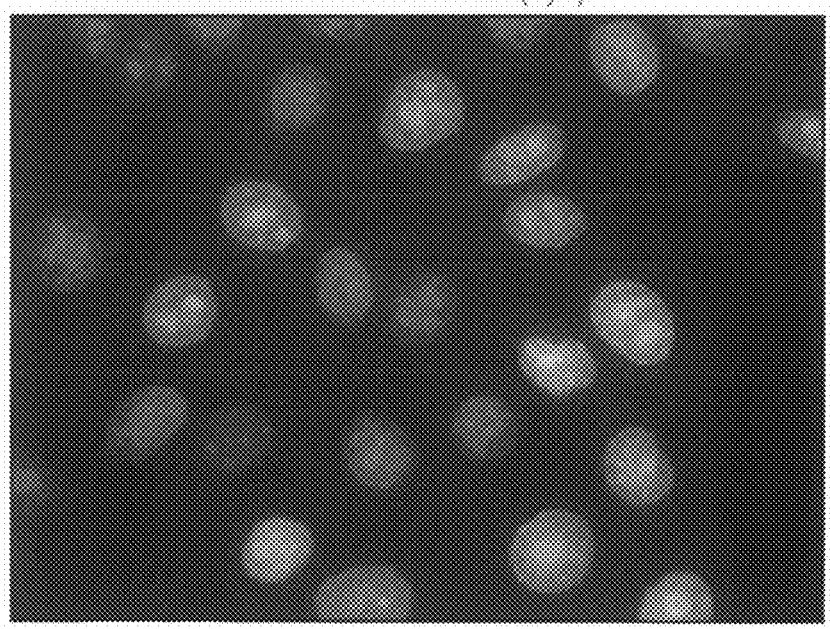

Compound 43 clearly has an advantage over DRAQ5 for multiplexing with far-red emitting dyes. Draq5 emits in both the Cy5 and the Texas Red filters as seen in FIG. 14. This prevents the use of another fluorescent tag that would emit in the opposite channel. As seen in FIG. 13 and in Table 5 above, Compound 43 emits almost entirely in the Texas Red channel, which leaves the Cy5 channel open for use of another fluorescent dye, such as Cy5 labeled Annexin V, Phycoerythrin-Cy5 (PE-Cy5), Alexafluor 660, Alexafluor 680, or Spectrum FarRed conjugates.

Many obvious variations will be suggested to those of ordinary skill in the art in light of the above detailed descriptions of the present invention. All such obvious variations are fully contemplated and are embraced by the scope and spirit of the present invention as set forth in the claims that now follow.

What is claimed is:

1. A compound comprising the structure

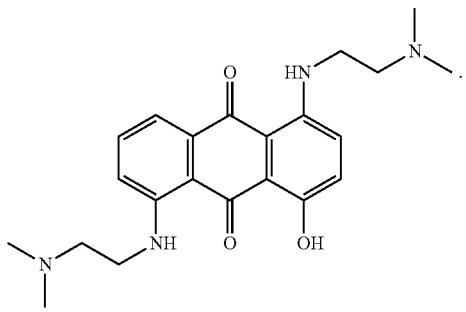

2. A method of identifying the location or position of a nucleus of a cell of interest, the method comprising the steps of:
   (A) providing
      (i) said cell of interest; and
      (ii) the compound

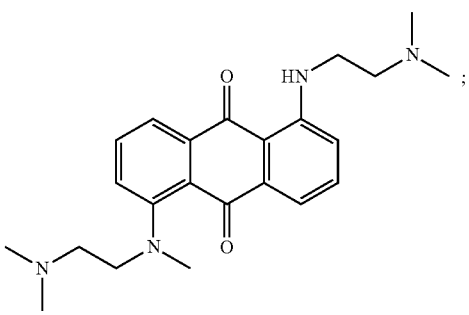

(B) incubating said cell of interest with said compound; and
(C) identifying the location or position of said nucleus.

3. The method of claim 2, further comprising the step of washing the cell after said incubating step and prior to said identifying step.

4. The method of claim 2, further comprising the step of fixing said cell of interest prior to said incubating step.

5. The method of claim 2, wherein said identifying step is carried out by detecting a fluorescent signal generated from said compound.

6. The method of claim 5, wherein said fluorescent signal is detected by a means comprising a fluorescence microscope, a flow cytometer, a confocal microscope, a fluorometer, a microplate reader, a high-content cell analysis system, a high-content cell screening system, a laser-scanning cytometer, or a combination of any of the foregoing.

7. The method of claim 2, further comprising providing one or more detection reagents which are different from said compound.

8. The method of claim 7, wherein said one or more detection reagents are applied in said incubating step at the same time with said cell of interest and said compound.

9. The method of claim 7, wherein said one or more detection reagents are applied to said cell of interest prior to said incubating step with said compound.

10. The method of claim 7, wherein said one or more detection reagents are applied to said cell of interest after said incubating step with said compound.

11. The method of claim 7, wherein said one or more detection reagents comprise an antibody, a lectin, an avidin, a streptavidin, a fluorescent protein, a fluorescent stain, a fusion tag, a phospholipid-binding protein, or a combination of any of the foregoing.

12. The method of claim 11, wherein said one or more detection reagents comprise a fluorescent protein or fluorescent stain that comprises 4',6-diamidino-2-phenylindole (DAPI), 5-Hydroxytryptamine (HAT), Acridine Orange, Acridine Yellow, Alexa Fluor dye, Blue Fluorescent Protein, BODIPY dye, Cascade Blue, Coelenterazine, Coumarin, Cyan Fluorescent Protein, Cyanine dye, Dansyl dye, Erythrosin, Far-red Fluorescent Proteins, FLUO 3, Fluorescein, FURA 2, Green Fluorescent Protein, Hoechst dye, INDO 1, JC-1 dye, Lucifer Yellow, Nile Red, Oregon Green dye, Propidium Iodide, QUIN 2, Red Fluorescent Protein, Rhodamine dye, R-Phycoerythrin, R-Phycoerythrin-Texas Red, SNARF, Texas Red, UV-excitable Green Fluorescent Protein, Yellow Fluorescent Protein, or a combination of any of the foregoing.

13. The method of claim 11, wherein said one or more detection reagents comprises a fluorescent protein or fluorescent stain that comprises Cy5, Phyocoerythrin-Cy5 (PE-Cy5), Alexafluor 660, Alexafluor 680, a Spectrum FarRed conjugate, or a combination of any of the foregoing.

14. The method of claim 2, wherein said cells of interest are contained in a sample.

* * * * *